(12) United States Patent
Moberg

(10) Patent No.: US 7,063,684 B2
(45) Date of Patent: Jun. 20, 2006

(54) DRIVE SYSTEM SEAL

(75) Inventor: Sheldon B. Moberg, Thousand Oaks, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 345 days.

(21) Appl. No.: 10/369,438

(22) Filed: Feb. 19, 2003

(65) Prior Publication Data
US 2003/0167039 A1    Sep. 4, 2003

Related U.S. Application Data

(63) Continuation-in-part of application No. 09/698,783, filed on Oct. 27, 2000, now Pat. No. 6,800,071, which is a continuation-in-part of application No. 09/429,352, filed on Oct. 28, 1999, now Pat. No. 6,248,093.

(51) Int. Cl.
*A61M 37/00*    (2006.01)

(52) U.S. Cl. .................. 604/155; 604/152; 128/DIG. 1; 128/DIG. 12

(58) Field of Classification Search ................ 604/181, 604/221, 213, 218, 187, 220, 228, 224, 235, 604/152, 154, 131, 151, 155, 121, 123; 128/DIG. 1, 128/DIG. 12, DIG. 13; 600/432
See application file for complete search history.

(56) References Cited

U.S. PATENT DOCUMENTS

| 1,540,126 A | 6/1925 | Hein |
| 3,623,474 A | 11/1971 | Heilman et al. |
| 3,701,345 A | 10/1972 | Heilman et al. |
| 4,084,588 A | 4/1978 | Koenig |
| 4,267,836 A | 5/1981 | Whitney et al. |
| 4,444,546 A | 4/1984 | Pazemenas |
| 4,468,221 A | 8/1984 | Mayfield |
| 4,498,904 A | 2/1985 | Turner et al. |
| 4,562,751 A | 1/1986 | Nason et al. |
| 4,568,335 A | 2/1986 | Updike et al. |
| 4,576,211 A | 3/1986 | Valentini et al. |
| 4,585,439 A | 4/1986 | Michel |
| 4,601,491 A | 7/1986 | Bell, Jr. et al. |

(Continued)

FOREIGN PATENT DOCUMENTS

DE    2240694    8/1972

(Continued)

OTHER PUBLICATIONS

International Search Report for International Application No. PCT/US00/29657.

(Continued)

*Primary Examiner*—Cris Rodriguez
(74) *Attorney, Agent, or Firm*—Medtronic MiniMed, Inc

(57) ABSTRACT

A pump for dispensing a fluid from a reservoir provides a drive system seal within the pump. The pump includes a reservoir cavity adapted to receive the reservoir, and a drive system. The pump also includes at least one plunger slider having one end coupled to the drive system and the other end coupled to the reservoir. The plunger slider is adapted to translate from a retracted position to an extended position to dispense the fluid from the reservoir in response to actuation by the drive system. The pump further includes a sealing ring mounted around the plunger slider, and a spring disposed within the sealing ring. The sealing ring with the spring disposed therein is adapted to allow the plunger slider to translate from the retracted position to the extended position, and to prevent entry of fluid from the reservoir cavity into the drive system.

20 Claims, 19 Drawing Sheets

U.S. PATENT DOCUMENTS

| | | | |
|---|---|---|---|
| 4,619,646 A | 10/1986 | Hernandez et al. | |
| 4,652,260 A | 3/1987 | Fenton, Jr. et al. | |
| 4,678,408 A | 7/1987 | Nason et al. | |
| 4,685,903 A | 8/1987 | Cable et al. | |
| 4,710,179 A | 12/1987 | Haber et al. | |
| 4,744,786 A * | 5/1988 | Hooven | 604/143 |
| 4,744,790 A | 5/1988 | Janowski et al. | |
| 4,747,824 A | 5/1988 | Spinello | |
| 4,749,109 A | 6/1988 | Kamen | |
| 4,838,857 A | 6/1989 | Strowe et al. | |
| 4,952,205 A | 8/1990 | Mauerer et al. | |
| 5,080,653 A | 1/1992 | Voss et al. | |
| 5,085,638 A * | 2/1992 | Farbstein et al. | 604/110 |
| 5,097,122 A | 3/1992 | Colman et al. | |
| 5,121,019 A | 6/1992 | Pradler | |
| 5,219,099 A | 6/1993 | Spence et al. | |
| 5,244,461 A | 9/1993 | Derlien | |
| 5,254,096 A | 10/1993 | Rondelet et al. | |
| 5,279,606 A | 1/1994 | Haber et al. | 604/403 |
| 5,292,306 A | 3/1994 | Wynkoop et al. | |
| D347,894 S | 6/1994 | Hansen et al. | |
| 5,370,630 A * | 12/1994 | Smidebush et al. | 604/209 |
| 5,389,078 A | 2/1995 | Zalesky et al. | |
| 5,411,488 A | 5/1995 | Pagay et al. | 604/218 |
| 5,505,709 A | 4/1996 | Funderburk et al. | |
| 5,545,152 A | 8/1996 | Funderburk et al. | |
| 5,549,574 A | 8/1996 | Townsend | |
| 5,554,134 A | 9/1996 | Bonnichsen | |
| 5,599,323 A | 2/1997 | Bonnichsen et al. | |
| 5,611,785 A | 3/1997 | Mito et al. | |
| D380,262 S | 6/1997 | Van Funderburk et al. | |
| 5,637,095 A | 6/1997 | Nason et al. | |
| 5,647,853 A | 7/1997 | Feldmann et al. | |
| 5,722,545 A | 3/1998 | Rinne | |
| 5,735,825 A | 4/1998 | Stevens et al. | |
| 5,779,675 A | 7/1998 | Reilley et al. | |
| 5,873,861 A | 2/1999 | Hitchins et al. | 604/152 |
| 5,902,276 A | 5/1999 | Namey, Jr. et al. | 604/218 |
| 5,919,167 A | 7/1999 | Mulhauser et al. | 604/131 |
| 5,947,929 A | 9/1999 | Trull | 604/131 |
| 5,947,935 A | 9/1999 | Rhinehart et al. | |
| 6,004,300 A | 12/1999 | Butcher et al. | 604/218 |
| 6,090,081 A | 7/2000 | Sudo et al. | 604/218 |
| 6,248,093 B1 | 6/2001 | Moberg | 604/131 |
| 6,258,068 B1 * | 7/2001 | Kirchhofer et al. | 604/208 |
| 6,362,591 B1 * | 3/2002 | Moberg | 318/685 |
| 6,432,089 B1 | 8/2002 | Kakimi et al. | 604/218 |
| 6,436,075 B1 | 8/2002 | Liao | 604/181 |
| 6,447,487 B1 | 9/2002 | Canel | 604/131 |
| 6,485,465 B1 * | 11/2002 | Moberg et al. | 604/154 |
| 6,620,137 B1 * | 9/2003 | Kirchhofer et al. | 604/218 |
| 6,827,708 B1 * | 12/2004 | Kirchhofer | 604/187 |

FOREIGN PATENT DOCUMENTS

| | | |
|---|---|---|
| EP | 0544653 | 1/1989 |
| FR | 2547201 | 6/1983 |
| FR | 2750961 | 7/1996 |
| WO | 9800157 | 10/1998 |
| WO | 9910032 | 3/1999 |

OTHER PUBLICATIONS

Annex to Form PCT/ISA/206 Communication Relating to the Results of the Partial International Search for International Application No. PCT/US00/29657.

PCT Application PCT/US99/25414 Search Report Mailed Feb. 2, 2000.

PCT Application PCT/US99/25413 Search Report Mailed Mar. 7, 2000.

H-TRONplus (Insulin Pump) Reference Manual. by Disetronic.

* cited by examiner

DRIVE SYSTEM SEAL

RELATED APPLICATIONS

This application is a continuation-in-part of U.S. patent application Ser. No. 09/698,783, filed Oct. 27, 2000, now U.S. Pat. No. 6,800,071, which is a continuation-in-part of U.S. patent application Ser. No. 09/429,352, filed Oct. 28, 1999 and now U.S. Pat. No. 6,248,093 issued Jun. 19, 2001.

BACKGROUND OF THE INVENTION

1. Field of the Invention

This invention relates generally to improvements in infusion pumps such as those used for controlled delivery of medication to a patient. Additionally, this invention relates to an improved drive system seal for use in such infusion pumps.

2. Description of the Related Art

Infusion pump devices and systems are relatively well-known in the medical arts, for use in delivering or dispensing a prescribed medication such as insulin to a patient. In one form, such devices comprise a relatively compact pump housing adapted to receive a syringe or reservoir carrying a prescribed medication for administration to the patient through infusion tubing and an associated catheter or infusion set.

The infusion pump includes a small drive motor connected via a lead screw assembly for motor-driven advancement of a reservoir piston to administer the medication to the user. Programmable controls can operate the drive motor continuously or at periodic intervals to obtain a closely controlled and accurate delivery of the medication over an extended period of time. Such infusion pumps are used to administer insulin and other medications, with exemplary pump constructions being shown and described in U.S. Pat. Nos. 4,562,751; 4,678,408; 4,685,903; 5,080,653 and 5,097,122, which are incorporated by reference herein.

Infusion pumps of the general type described above have provided significant advantages and benefits with respect to accurate delivery of medication or other fluids over an extended period of time. The infusion pump can be designed to be extremely compact as well as water resistant, and may thus be adapted to be carried by the user, for example, by means of a belt clip or the like. As a result, important medication can be delivered to the user with precision and in an automated manner, without significant restriction on the user's mobility or life-style, including in some cases the ability to participate in water sports.

These pumps often incorporate a drive system which uses a lead screw coupled to motors. The motors can be of the DC, stepper or solenoid varieties. These drive systems provide an axial displacement of the syringe or reservoir piston thereby dispensing the medication to the user. Powered drive systems are advantageous since they can be electronically controlled to deliver a predetermined amount of medication by means well known in the art.

In the operation of these pump systems, the reservoir piston will be fully advanced when virtually all of the fluid in the reservoir has been dispensed. Correspondingly, the axial displacement of the motor lead screw is also typically fully displaced. In order to insert a new reservoir which is full of fluid, it is necessary to restore the lead screw to its original position. Thus the lead screw will have to be rewound or reset.

DC motors and stepper motors are advantageous over solenoid motors in that the former are typically easier to operate at speeds that allow rewinding the drive system electronically. Solenoid based drive systems, on the other hand, often must be reset manually, which in turn makes water resistant construction of the pump housing more difficult.

Lead screw drive systems commonly use several gears which are external to the motor. FIG. 1 shows such a lead screw arrangement which is known in the art. A motor 101 drives a lead screw 102 which has threads which are engaged with a drive nut 103. Thus the rotational force of the lead screw 102 is transferred to the drive nut 103 which causes it to move in an axial direction d. Because the drive nut 103 is fixably attached to a reservoir piston 104 by a latch arm 110, it likewise will be forced in an axial direction d', parallel to direction d, thus dispensing the fluid from a reservoir 105 into an infusion set 106. The lead screw 102 is mounted on a bearing 111 which provides lateral support. The lead screw 102 extends through the bearing and comes in contact with the occlusion detector 108. One known detector uses an "on/off" pressure limit switch.

Should an occlusion arise in the infusion set 106 tubing, a back pressure will build up in the reservoir 105 as the piston 104 attempts to advance. The force of the piston 104 pushing against the increased back pressure will result in an axial force of the lead screw 102 driving against the detector 108. If the detector 108 is a pressure limit switch, then an axial force that exceeds the set point of the pressure limit switch 108 will cause the switch to close thus providing an electrical signal through electrical leads 109 and to the system's electronics. This, in turn, can provide a system alarm. The entire assembly can be contained in a water resistant housing 107.

FIG. 2 shows a different drive system and lead screw arrangement which also is known in the art. In this arrangement, a motor 201 (or a motor with an attached gear box) has a drive shaft 201a which drives a set of gears 202. The torque is then transferred from the gears 202 to a lead screw 203. The threads of the lead screw 203 are engaged with threads [not shown] in a plunger slide 204. Thus the torque of the lead screw 203 is transferred to the slide 204 which causes it to move in an axial direction d', parallel to the drive shaft 201a of the motor 201. The slide 204 is in contact with a reservoir piston 205 which likewise will be forced to travel in the axial direction d' thus dispensing fluid from a reservoir 206 into an infusion set 207. The lead screw 203 is mounted on a bearing 209 which provides lateral support. The lead screw 203 can extend through the bearing to come in contact with an occlusion detector 210. As before, if the detector 210 is a pressure limit switch, then an axial force that exceeds the set point of the pressure limit switch 210 will cause the switch to close thus providing an electrical signal through electrical leads 211 and to the system's electronics. This, in turn, can provide a system alarm. The assembly can be contained in a water resistant housing 208.

As previously noted, these lead screw drive systems use gears which are external to the motor. The gears are in combination with a lead screw with external threads which are used to drive the reservoir's piston. This external arrangement occupies a substantial volume which can increase the overall size of the pump. Moreover, as the number of drive components, such as gears and lead screw, increases, the torque required to overcome inherent mechanical inefficiencies can also increase. As a result, a motor having sufficient torque also often has a consequent demand for increased electrical power.

Yet another known drive is depicted in FIGS. 3a and 3b. A reservoir 301 fits into the unit's housing 302. Also shown are the piston member 303 which is comprised of an elongated member with a substantially circular piston head 304 for displacing the fluid in the reservoir 301 when driven by the rotating drive screw 305 on the shaft (not visible) of the drive motor 306.

As is more clearly shown in FIG. 3*b*, the reservoir 301, piston head 304 and piston member 303 comprise an integrated unit which is placed into the housing 302 (FIG. 3*a*). The circular piston head 304 displaces fluid in the reservoir upon axial motion of the piston member 303. The rearward portion of the piston member 303 is shaped like a longitudinal segment of a cylinder as shown in FIG. 3*b* and is internally threaded so that it may be inserted into a position of engagement with the drive screw 305. The drive screw 305 is a threaded screw gear of a diameter to mesh with the internal threads of the piston member 303. Thus the motor 306 rotates the drive screw 305 which engages the threads of the piston member 303 to displace the piston head 304 in an axial direction d.

While the in-line drive system of FIG. 3*a* achieves a more compact physical pump size, there are problems associated with the design. The reservoir, piston head and threaded piston member constitute an integrated unit. Thus when the medication is depleted, the unit must be replaced. This results in a relatively expensive disposable item due to the number of components which go into its construction.

Moreover the drive screw 305 and piston head 304 of FIG. 3*a* are not water resistant. Because the reservoir, piston head and threaded piston member are removable, the drive screw 305 is exposed to the atmosphere. Any water which might come in contact with the drive screw 305 may result in corrosion or contamination which would affect performance or result in drive failure.

The design of FIG. 3*a* further gives rise to problems associated with position detection of the piston head 304. The piston member 303 can be decoupled from the drive screw 305. However, when another reservoir assembly is inserted, it is not known by the system whether the piston head 304 is in the fully retracted position or in some intermediate position. Complications therefore are presented with respect to providing an ability to electronically detect the position of the piston head 304 in order to determine the extent to which the medication in reservoir 301 has been depleted.

The construction of pumps to be water resistant can give rise to operational problems. As the user travels from various elevations, such as might occur when traveling in an air plane, or as the user engages in other activities which expose the pump to changing atmospheric pressures, differential pressures can arise between the interior of the air tight/water-resistant pump housing and the atmosphere. Should the pressure in the housing exceed external atmospheric pressure, the resulting forces could cause the reservoir piston to be driven inward thus delivering unwanted medication.

Thus it is desirable to have an improved, compact, water resistant drive system which permits safe user activity among various atmospheric pressures and other operating conditions. Moreover it is desirable to have improved medication reservoir pistons for use with such drive systems.

SUMMARY OF THE PREFERRED EMBODIMENTS

Embodiments of the present invention provide an improved apparatus for dispensing a medication fluid from a reservoir adapted to contain the fluid. In accordance with an embodiment of the present invention, the apparatus includes a reservoir cavity adapted to receive the reservoir, a drive system, and at least one plunger slider. One end of the at least one plunger slider is coupled to the drive system, and the other end of the at least one plunger slider is releasably coupled to the reservoir. Also, the at least one plunger slider is adapted to translate from a retracted position to an extended position to dispense the fluid from the reservoir in response to actuation by the drive system. The apparatus further includes a sealing ring mounted around the at least one plunger slider, and a spring disposed within the sealing ring. The sealing ring with the spring disposed therein is adapted to allow the at least one plunger slider to translate from the retracted position to the extended position, and also to prevent entry of fluid from the reservoir cavity into the drive system.

In particular embodiments, the sealing ring may be formed from Teflon or plastic. In other particular embodiments, the spring may be a leaf spring or a canted coil spring.

The sealing ring may have a proximate side and a distal side, with the proximate side being adjacent to the reservoir cavity. In some embodiments, the distal side of the sealing ring defines an opening leading into a cavity, and the spring is inserted into the cavity in the sealing ring. In alternative embodiments, the proximate side defines an opening leading into a cavity, and the spring is inserted into the cavity in the sealing ring. In further alternative embodiments, the sealing ring has no openings, and the spring is enclosed within the sealing ring.

In other embodiments, the drive system includes a drive motor and a drive gear. The drive gear is positioned to be rotatably actuated by the drive shaft of the drive motor. Additionally, the drive gear has internal threads, and the at least one plunger slider has external threads positioned to be engaged by the internal threads of the drive gear. The at least one plunger slider is adapted to be linearly actuated by rotation of the internal threads of the drive gear. In alternative embodiments, the drive gear has external threads, and the at least one plunger slider has internal threads positioned to be engaged by the external threads of the drive gear. The at least one plunger slider is adapted to be linearly actuated by rotation of the external threads of the drive gear. In yet other alternative embodiments, the drive system includes a drive motor having a rotating drive shaft, and a gearbox coupled to the drive shaft of the drive motor. The at least one plunger slider is coupled to the gearbox and adapted to translate from the retracted position to the extended position in response to rotation of the drive shaft of the drive motor.

In accordance with another embodiment of the present invention, an apparatus for dispensing a medication fluid from a reservoir adapted to contain the fluid includes a reservoir cavity adapted to receive the reservoir, a drive motor, a drive gear, and at least one plunger slider. The drive gear is coupled to the drive motor and adapted to be rotatably actuated by the drive motor. One end of the at least one plunger slider is coupled to the drive gear, and the other end of the at least one plunger slider is releasably coupled to the reservoir. Also, the at least one plunger slider is adapted to translate from a retracted position to an extended position to dispense the fluid from the reservoir in response to rotation by the drive gear. The apparatus further includes a sealing ring mounted around the at least one plunger slider, and a spring disposed within the sealing ring. The sealing ring with the spring disposed therein is adapted to allow the at least one plunger slider to translate from the retracted position to the extended position, and also to prevent entry of fluid from the reservoir cavity into the drive system.

In particular embodiments, the sealing ring may be formed from Teflon or plastic. In other particular embodiments, the spring may be a leaf spring or a canted coil spring.

The sealing ring may have a proximate side and a distal side, with the proximate side being adjacent to the reservoir cavity. In some embodiments, the distal side of the sealing ring defines an opening leading into a cavity, and the spring is inserted into the cavity in the sealing ring. In alternative embodiments, the proximate side defines an opening leading into a cavity, and the spring is inserted into the cavity in the sealing ring. In further alternative embodiments, the sealing ring has no openings, and the spring is enclosed within the sealing ring.

In other embodiments, the drive gear has internal threads, and the at least one plunger slider has external threads positioned to be engaged by the internal threads of the drive gear. The at least one plunger slider is adapted to be linearly actuated by rotation of the internal threads of the drive gear. In alternative embodiments, the drive gear has external threads, and the at least one plunger slider has internal threads positioned to be engaged by the external threads of the drive gear. The at least one plunger slider is adapted to be linearly actuated by rotation of the external threads of the drive gear.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 3b shows the details of a disposable reservoir with the piston and drive member withdrawn of the lead-screw drive mechanism of FIG. 3a.

FIG. 15b is an elevation view of the reservoir piston of FIG. 15a.

FIG. 16b is a top plan view of the piston insert of FIG. 16a.

DETAILED DESCRIPTION OF THE PREFERRED EMBODIMENTS

Figure 1:
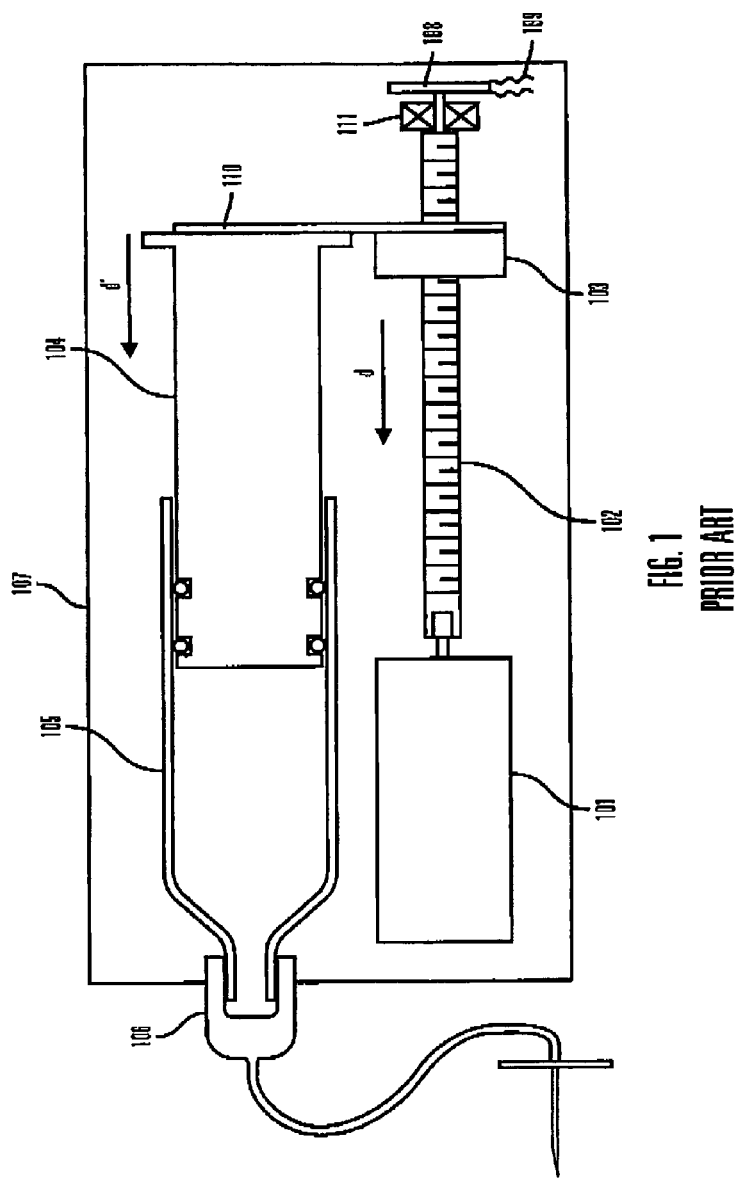
FIG. 1 is a side plan view of a conventional lead-screw drive mechanism.

In the following description, reference is made to the accompanying drawings which form a part hereof and which illustrate several embodiments of the present inventions. It is understood that other embodiments may be utilized and structural and operational changes may be made without departing from the scope of the present inventions.

As shown in the drawings for purposes of illustration, some aspects of the present inventions are directed to a drive mechanism for an infusion pump for medication or other fluids. In preferred embodiments, a releasable coupler couples an in-line drive to a plunger or piston of a reservoir to dispense fluids, such as medications, drugs, vitamins, vaccines, hormones, water or the like. However, it will be recognized that further embodiments of the invention may be used in other devices that require compact and accurate drive mechanisms. Details of the inventions are further provided in co-pending U.S. patent application Ser. No. 09/429,352 filed Oct. 29, 1999, and U.S. Provisional Patent Application Ser. No. 60/106,237 filed Oct. 29, 1998, both of which are incorporated herein by reference in their entireties.

In addition, the reservoir piston includes features which provide greater stiffness against fluid back pressure thus reducing system compliance. The piston further includes a threaded attachment feature which permits a releasable yet secure coupling between the reservoir piston and the in-line drive.

Figure 4:
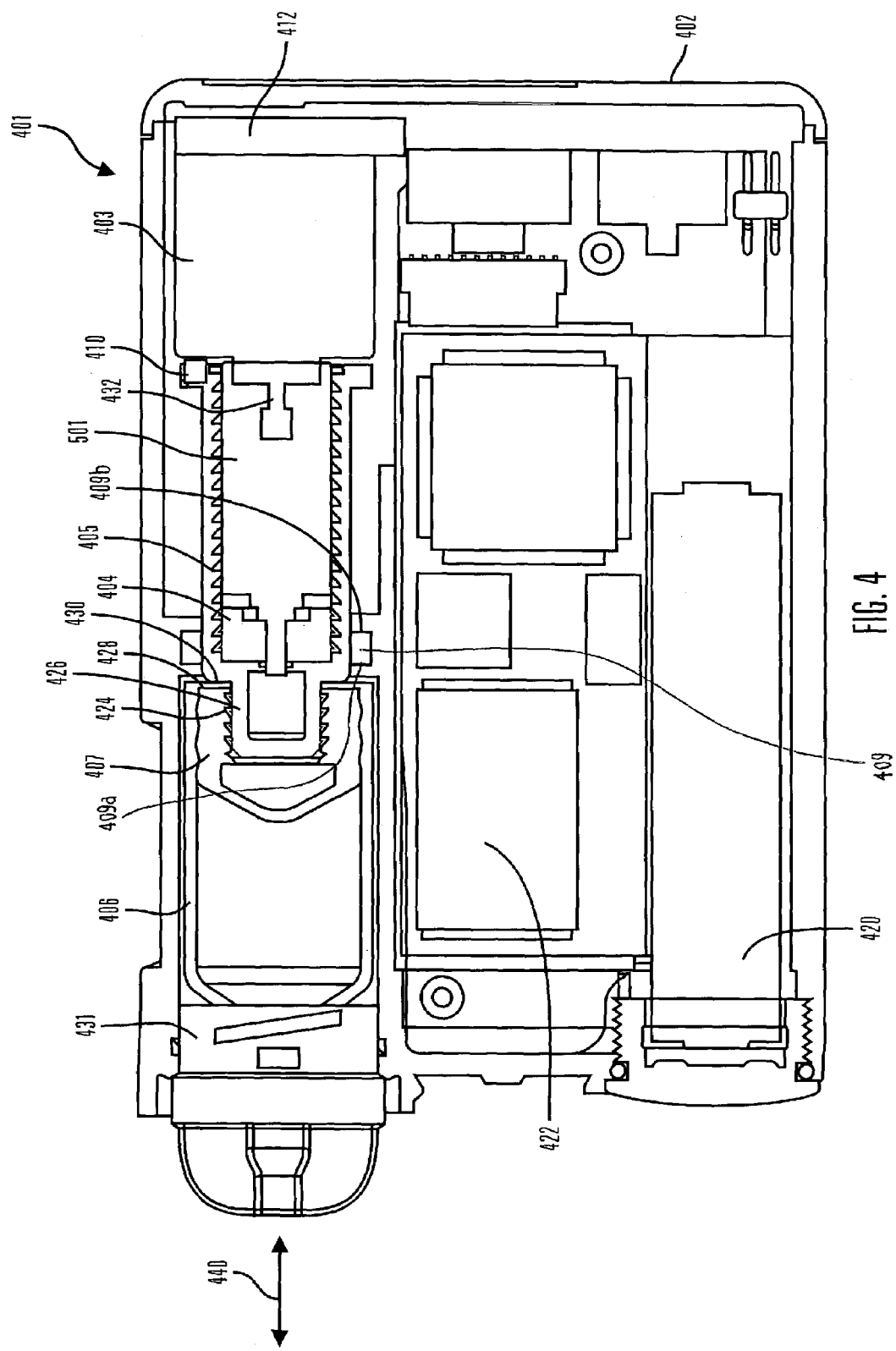
FIG. 4 is a side plan, cut-away view of a drive mechanism in a retracted position in accordance with an embodiment of the present invention.

FIG. 4 shows a side plan, cut-away view of an infusion pump drive mechanism according to one embodiment of the inventions, in which a housing 401, containing a lower section 402 for a power supply 420 and electronic control circuitry 422, accommodates a driving device, such as a motor 403 (e.g., a solenoid, stepper or DC motor), a first drive member, such as an externally threaded drive gear or screw 404, a second drive member, such as an internally threaded plunger gear or slide 405, and a removable vial or reservoir 406. The reservoir 406 includes a plunger or piston assembly 407 with O-rings or integral raised ridges for forming a water and air tight seal. The reservoir 406 is secured into the housing 401 with a connector 431 which also serves as the interface between the reservoir 406 and the infusion set tubing (not shown). In one embodiment, the reservoir piston assembly 407 is coupled to a linear actuation member, such as the plunger slide 405, by a releasable coupler. In the illustrated embodiment, the coupler includes a female portion 424 which receives a male portion 426 carried by the plunger slide 405. The female portion 424 is positioned at the end face 428 of the piston assembly 407 and includes a threaded cavity which engages the threads of a male screw extending from the end 430 of the plunger slide 405.

While certain embodiments of the present inventions are directed to disposable, pre-filled reservoirs, alternative embodiments may use refillable cartridges, syringes or the like. The cartridge can be pre-filled with insulin (or other drug or fluid) and inserted into the pump. Alternatively, the cartridge could be filled by the user using an adapter handle on the syringe-piston. After being filled, the handle is removed (such as by unscrewing the handle) so that the cartridge can be placed into the pump.

Referring again to FIG. 4, as the drive shaft 432 of the motor 403 rotates, the drive screw 404 drives the plunger slide 405 directly to obtain the axial displacement against the reservoir piston assembly 407 to deliver the predetermined amount of medication or liquid. When using a DC or stepper motor, the motor can be rapidly rewound when the reservoir is emptied or as programmed by the user.

Figure 6:
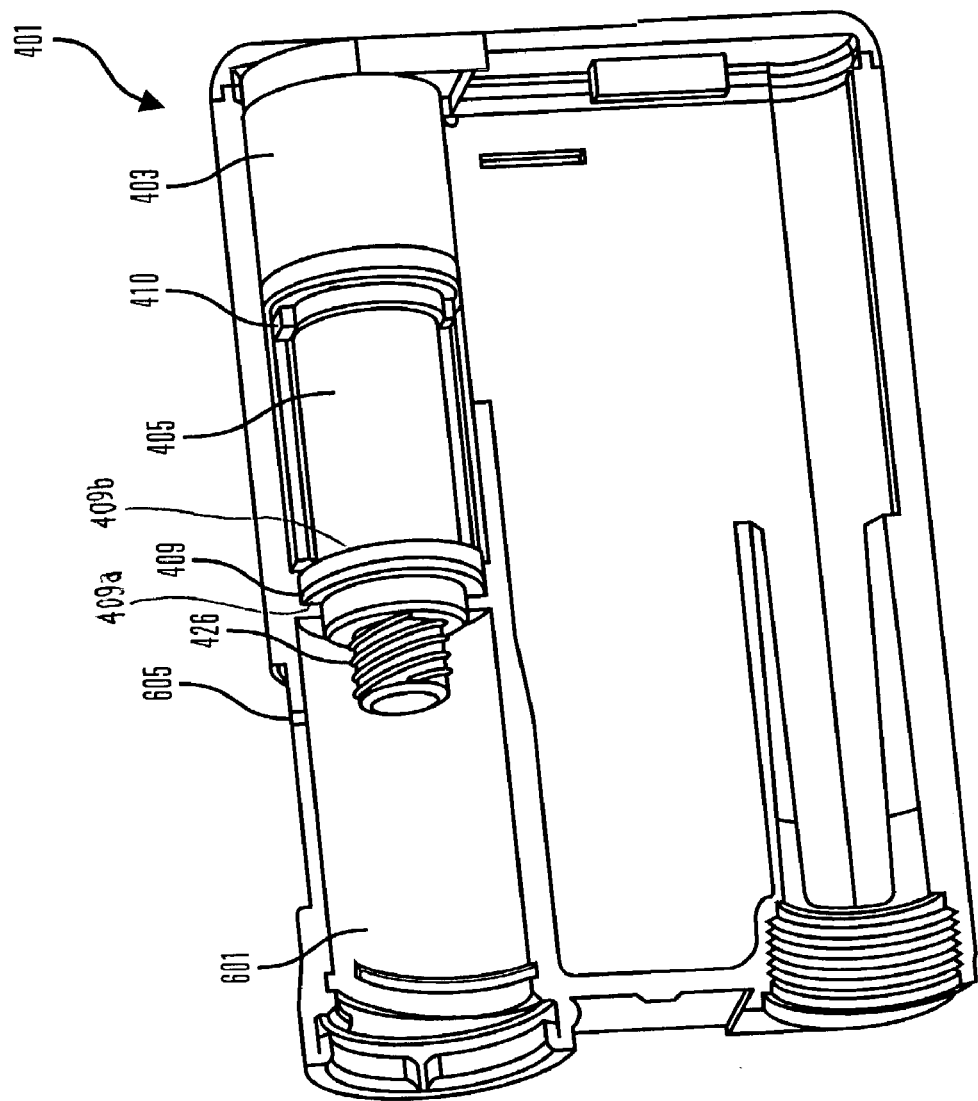
FIG. 6 is a cut-away perspective view of the drive mechanism of FIG. 4 in a retracted position.
Figure 6:
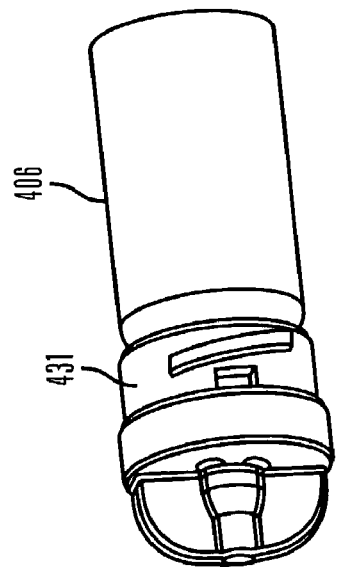
Figure 7A:
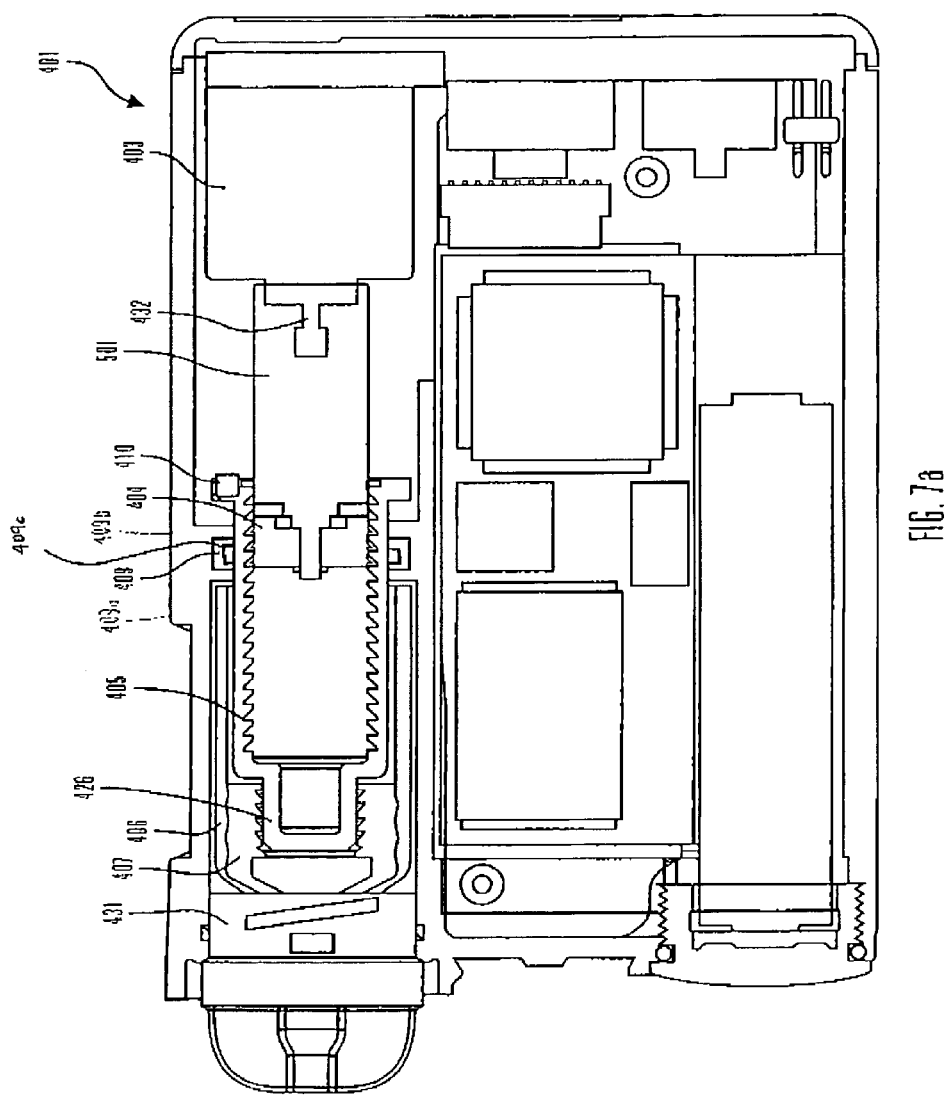
FIG. 7a is a side plan, cut-away view of the drive mechanism of FIG. 4 in an extended position.
Figure 7B:
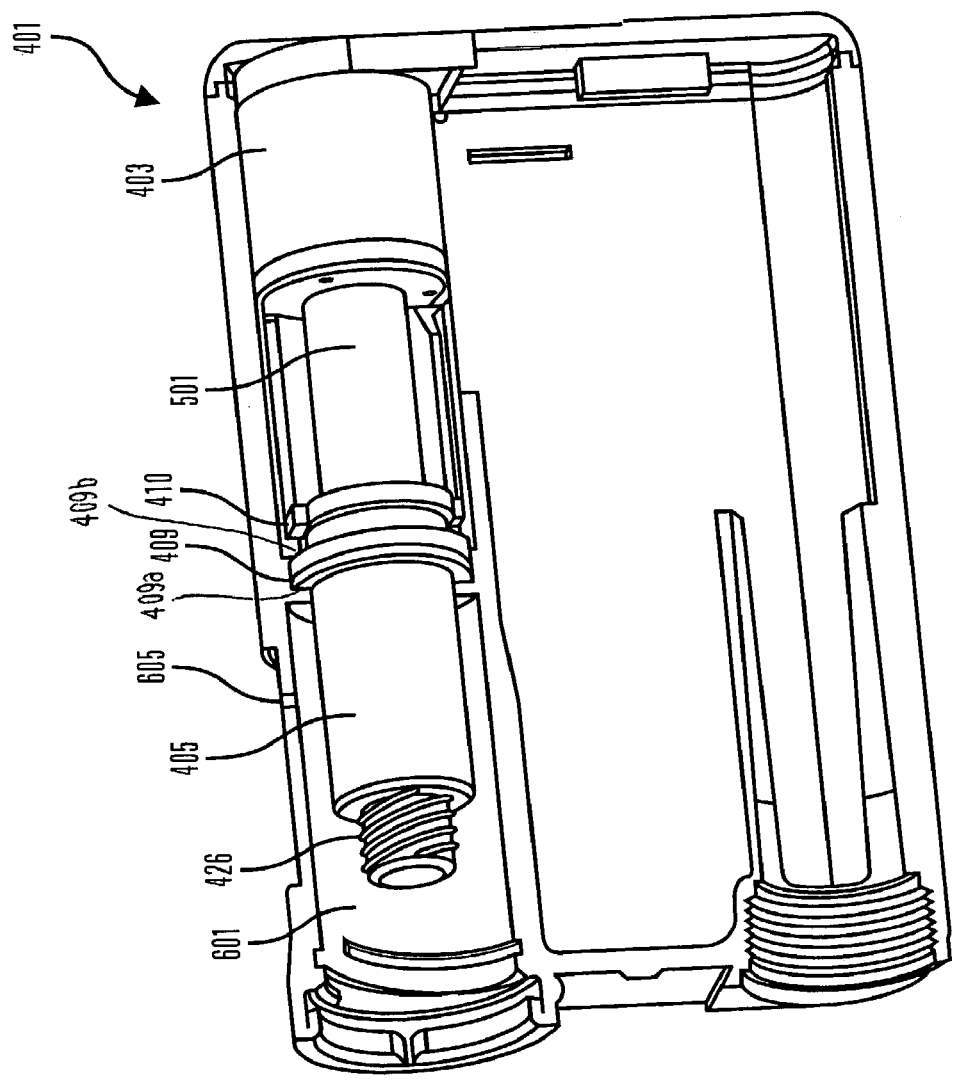
FIG. 7b is a cut-away perspective view of the drive mechanism of FIG. 4 in an extended position.
Figure 7B:
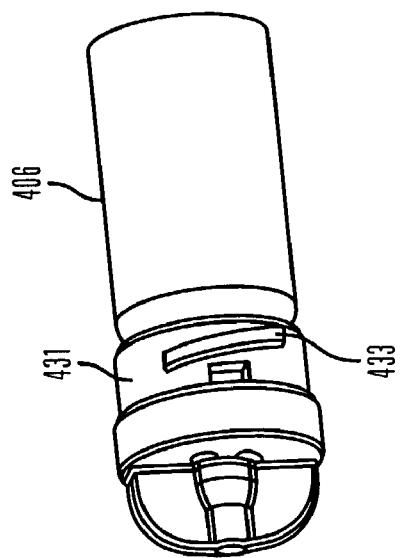

A sealing device 409 is adapted to be slidably mounted around the plunger slide 405, and allows the plunger slide 405 to move axially from a retracted position shown in FIG. 6 to a fully extended position in FIG. 7b, while maintaining a water resistant barrier between the cavity 601 holding the reservoir 406 and the motor 403. This prevents fluids and other contaminants from entering the drive system. In particular embodiments, the sealing device 409 may be a ring or collar 409, preferably formed from Teflon, plastic, or the like. The ring 409 has a proximate side 409a and a distal side 409b. The proximate side 409a of the ring 409 is adjacent to the cavity 601 holding the reservoir 406, and is adapted to maintain the water resistant barrier between the cavity 601 holding the reservoir 406 and the motor 403. The distal side 409b of the ring 409 may have an opening leading into a cavity (not shown), and a spring 409c (FIG. 7a) such as a leaf spring, canted coil spring, or the like may be inserted into the cavity. Such springs are available from Bal Seal Engineering Co. Inc. and/or Parker Hannifin Corporation. Alternatively, the distal side 409b of the ring 409 may have no opening, but the proximate side 409a of the ring 409 may have an opening leading into a cavity (not shown), and a spring 409c (FIG. 7a) such as a leaf spring, canted coil spring, or the like may be inserted into the cavity. In further alternative embodiments, the distal side 409b of the ring 409 may have no opening, and the leaf spring, canted coil spring, or the like may be encased or enclosed within the ring 409. In other particular embodiments, the sealing device 409 may be an O-ring 409 formed from rubber or the like.

However, the ring with the leaf spring, canted coil spring, or the like inserted therein is preferred over the O-ring. As described in greater detail in U.S. patent application Ser. No. 09/819,208 filed Mar. 27, 2001, and now issued U.S. Pat. No. 6,485,465, and Ser. No. 09/428,411 filed Oct. 28, 1999, and now issued U.S. Pat. No. 6,362,591, which are herein incorporated by reference, the pump may have an occlusion detection system that includes a sensor (not shown), which uses the axial force on the plunger slide 405 as an indicator of pressure within the reservoir 406. Generally during fluid delivery, as the drive system exerts force on the plunger slide 405 to obtain axial displacement against the piston assembly 407 within the reservoir 406, the corresponding force on the sensor temporarily increases. As the fluid is delivered from the reservoir 406, the force on the sensor returns to a similar level as measured before fluid delivery was initiated.

When the plunger slide 405 is initially coupled to the reservoir piston assembly 407 within the reservoir 406 (e.g., after insertion of a newly filled or replacement reservoir 406), the drive system exerts force on the plunger slide 405 to obtain axial displacement through the O-ring and against the piston assembly 407. However, the O-ring tends to deform or displace, and as a result, the force exerted by the drive system initially does not obtain any axial displacement of the plunger slide 405 against the piston assembly 407. Several rotations of the motor 403 are initially required, and the force on the sensor continues to increase, before the force exerted by the drive system begins to obtain any axial displacement of the plunger slide 405 through the O-ring and against the piston assembly 407. Thus, this configuration is subject to an initial buildup of force on the sensor before the plunger slide 405 is axially displaced against the piston assembly 407, and the fluid is delivered from the reservoir 406.

By contrast, the ring with the leaf spring, canted coil spring, or the like inserted therein does not deform or displace. Consequently, as the drive system exerts force on the plunger slide 405, the plunger slide 405 is axially displaced through the ring and against the piston assembly 407. Thus, the ring with the leaf spring, canted coil spring, or the like inserted therein is not subject to an initial buildup of force on the sensor before the force exerted by the drive system on the plunger slide 405 obtains axial displacement against the piston assembly 407 within the reservoir 406, and the fluid is delivered from the reservoir 406. As a result, there is a better correlation between the pressure in the reservoir 406 and the force exerted on the sensor, which allows the use of more robust methods to detect an occlusion within the pump (for example, as described in U.S. patent application Ser. No. 09/819,208 filed Mar. 27, 2001, and now issued U.S. Pat. No. 6,485,465, which is herein incorporated by reference) and also reduces the amount of time required for the system to detect an occlusion within the pump.

An anti-rotation key 410 is affixed to the plunger slide 405 and is sized to fit within a groove (not shown) axially disposed in the housing 401. This arrangement serves to prevent motor and plunger slide rotation which might otherwise result from the torque generated by the motor 403 in the event that the friction of the sealing device 409 is not sufficient alone to prevent rotation.

The motor 403 is a conventional motor, such as a DC or stepper motor, and is journal mounted in the housing 401 by a system compliance mounting 412. A system compliance mount can be useful in aiding motor startup. Certain types of motors, such as stepper motors, may require a great deal of torque to initiate rotor motion when the rotor's initial at-rest position is in certain orientations with respect to the motor's housing. A motor which is rigidly mounted may not have enough power to develop the necessary starting torque. Including system compliance mounting permits the motor housing to turn slightly in response to high motor torque. This alters the orientation between the rotor and the housing such that less torque is required to initiate rotor motion. A compliance mount can include a rubberized mounting bracket. Alternatively, the mounting could be accomplished using a shaft bearing and leaf spring or other known compliance mountings.

Figure 5:
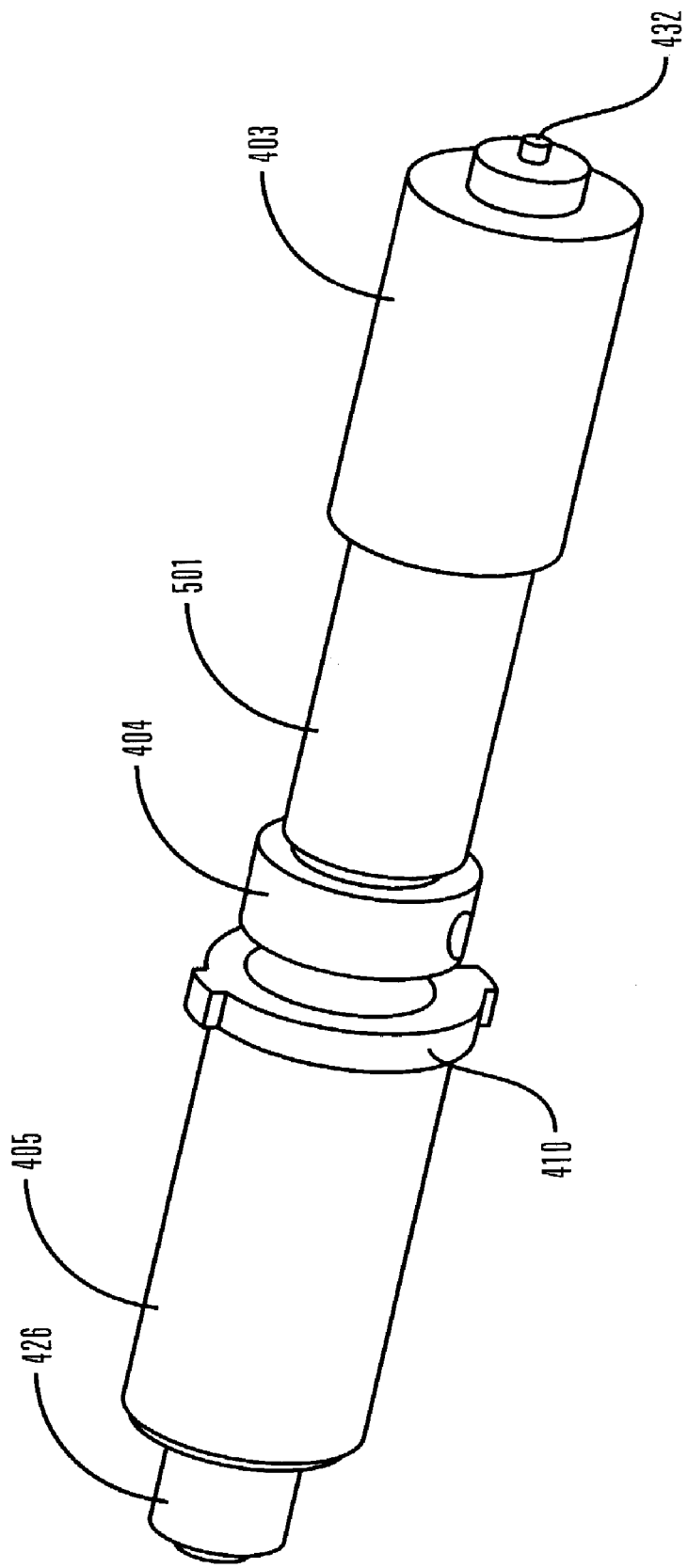
FIG. 5 is a perspective view of the in-line drive mechanism of FIG. 4 outside of the housing.

FIG. 5 shows a perspective view of the in-line drive mechanism of FIG. 4 outside of the housing. The plunger slide 405 (internal threads not shown) is cylindrically shaped and has the screw-shaped male portion 426 of the coupler attached to one end thereof. The anti-rotation key 410 is affixed to the opposite end of the slide 405. The drive screw 404 is of such a diameter as to fit within and engage the internal threads of the plunger slide 405 as shown in FIG. 4. A conventional gear box 501 couples the drive screw 404 to the drive shaft 432 of the motor 403.

FIGS. 4 and 6 show the infusion pump assembly with the plunger slide 405 in the retracted position. The reservoir 406 which may be full of medication or other fluid is inserted in a reservoir cavity 601 which is sized to receive a reservoir or vial. In the retracted position, the plunger slide 405 encloses the gear box 501 (not visible in FIG. 6) while the drive screw 404 (not visible in FIG. 6) remains enclosed within the plunger slide 405 but is situated close to the coupler.

The motor 403 may optionally include an encoder (not shown) which in conjunction with the system electronics can monitor the number of motor rotations. This in turn can be used to accurately determine the position of the plunger slide 405 thus providing information relating to the amount of fluid dispensed from the reservoir 406.

FIGS. 7a and 7b show the infusion pump assembly with the plunger slide 405 in the fully extended position. In this position, the plunger slide 405 has withdrawn from over the gear box 501 and advanced into the reservoir 406 behind the reservoir piston assembly 407. Accordingly, the plunger slide 405 is sized to fit within the housing of the reservoir 406, such that when the reservoir piston assembly 407 and the plunger slide 405 are in the fully extended position as shown, the reservoir piston assembly 407 has forced most, if not all, of the liquid out of the reservoir 406. As explained in greater detail below, once the reservoir piston assembly 407 has reached the end of its travel path indicating that the reservoir has been depleted, the reservoir 406 may be removed by twisting such that the threaded reservoir piston assembly 407 (not shown in FIG. 7b) disengages from the male portion 426 of the coupler.

In one embodiment, the motor drive shaft 432, gear box 501, drive screw 404, and plunger slide 405 are all coaxially centered within the axis of travel 440 (FIG. 4) of the reservoir piston assembly 407. In certain of the alternative embodiments, one or more of these components may be offset from the center of the axis of travel 440 and yet remain aligned with the axis of travel which has a length which extends the length of the reservoir 406.

Figure 8:
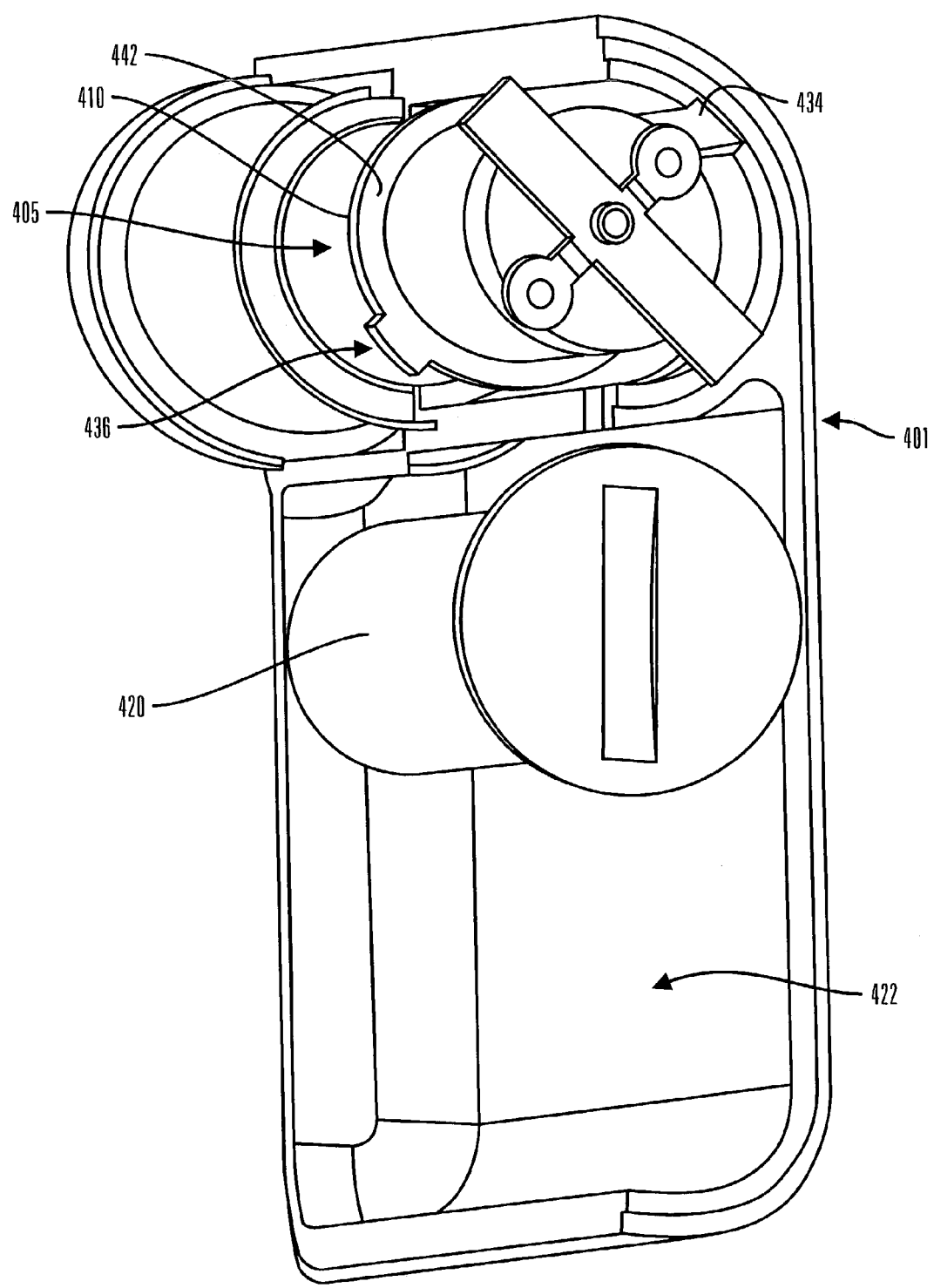
FIG. 8 is a cut-away perspective view of an anti-rotation device for use with the drive mechanism shown in FIG. 4.

FIG. 8 is a cut away perspective view of an anti-rotation device. The anti-rotation key 410 consists of a ring or collar 442 with two rectangular tabs 436 which are spaced 180° apart. Only one tab is visible in FIG. 8. The ring portion 442 of the key 410 surrounds and is attached to the end of the plunger slide 405 which is closest to the motor. Disposed in the housing 401 are two anti-rotation slots 434, only one of which is visible in FIG. 8. The anti-rotation slots 434 are sized to accept the rectangular tabs of the key 410. As the plunger slide 405 moves axially in response to the motor torque as previously described, the slots 434 will permit the key 410 to likewise move axially. However the slots 434 and the tabs 436 of the key 410 will prevent any twisting of the plunger slide 405 which might otherwise result from the torque generated by the motor.

Figure 9:
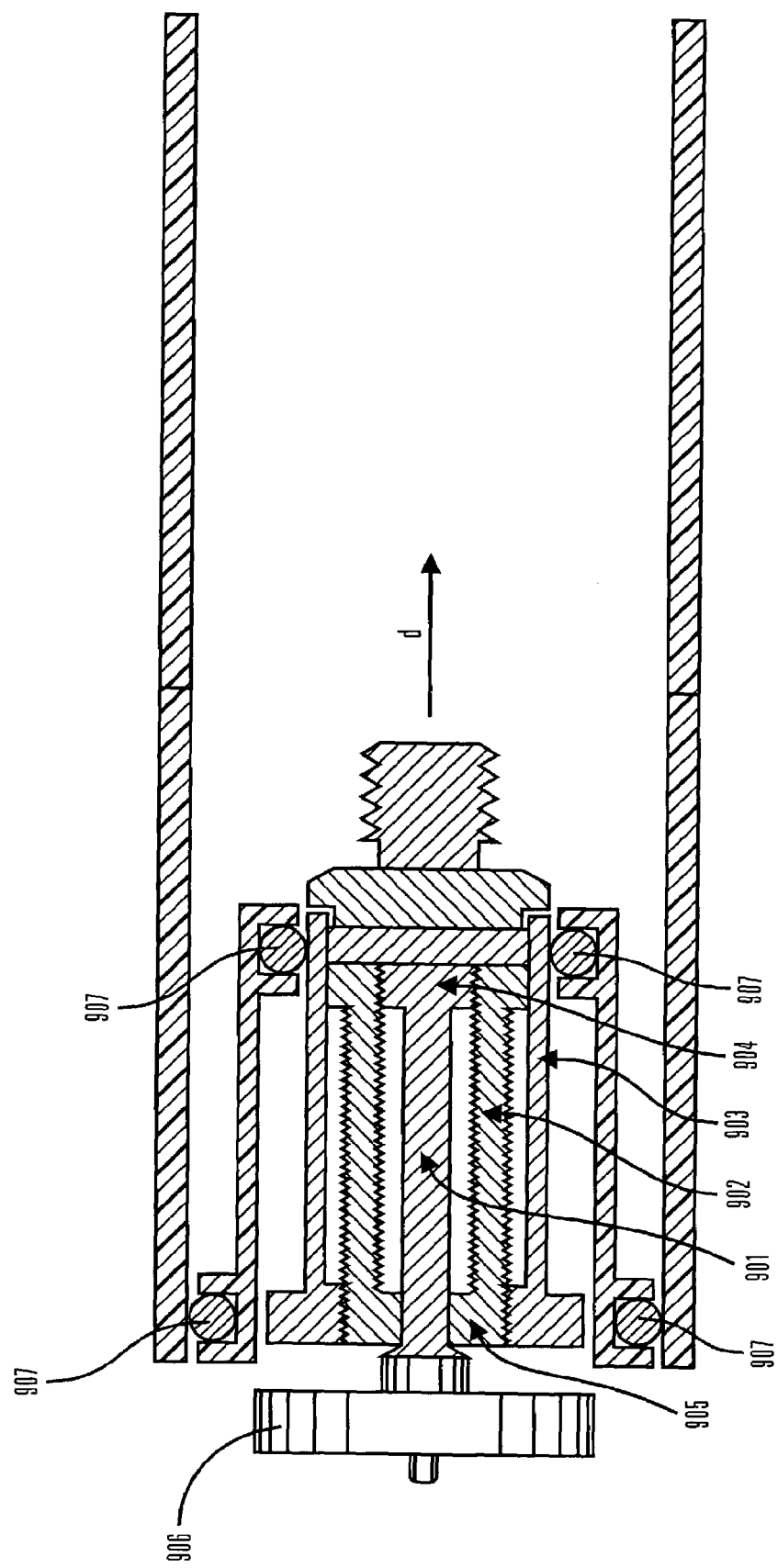
FIG. 9 is a cross-sectional view of a segmented (or telescoping) lead screw in accordance with an embodiment of the present invention.

FIG. 9 illustrates a split lead-screw (or plunger slide) design for use with a pump drive mechanism. The use of a split lead-screw or telescoping lead screw allows the use of an even smaller housing for the drive mechanism. A telescoping lead-screw formed from multiple segments allows the pump to minimize the dimensions of the drive mechanism, in either in-line or gear driven drive mechanisms.

An interior shaft 901 is rotated by a gear 906 which is coupled to a drive motor (not shown). This in turn extends a middle drive segment 902 by engaging with the threads of an internal segment 904. The middle segment 902 carries an outer segment 903 forward with it in direction d as it is extended to deliver fluid. When the middle segment 902 is fully extended, the internal segment 904 engages with a stop 905 on the middle segment 902 and locks it down from pressure with the threads between the middle and internal segments. The locked middle segment 902 then rotates relative to the outer segment 903 and the threads between the middle segment 902 and the outer segment 903 engage to extend the outer segment 903 in direction d to its full length.

The use of multiple segments is not limited to two or three segments; more may be used. The use of three segments reduces the length of the retracted lead-screw portion of the drive mechanism by half. In alternative embodiments, the outer segment may be connected to the motor and the inner segment may be the floating segment. In preferred embodiments, rings 907 with leaf springs, canted coil springs, or the like inserted therein as shown and described above in the embodiments of FIGS. 4 and 6–7b, or O-rings 907, are used to seal each segment relative to the other and to form a seal with the housing to maintain water sealing and integrity.

As previously noted, the construction of these pumps to be water resistant can give rise to operational problems. As the user engages in activities which expose the pump to varying atmospheric pressures, differential pressures can arise between the interior of the air tight/water-resistant housing and the atmosphere. Should the pressure in the housing exceed external atmospheric pressure, the resulting forces could cause the reservoir piston to be driven inward thus delivering unwanted medication. On the other hand, should the external atmospheric pressure exceed the pressure in the housing, then the pump motor will have to work harder to advance the reservoir piston.

To address this problem, a venting port is provided which resists the intrusion of moisture. Referring to FIG. 7b, venting is accomplished through the housing 401 into the reservoir cavity 601 via a vent port 605. The vent port can be enclosed by a relief valve (not shown) or covered with hydrophobic material. Hydrophobic material permits air to pass through the material while resisting the passage of water or other liquids from doing so, thus permitting water resistant venting. One embodiment uses a hydrophobic material such as Gore-Tex®, PTFE, HDPE, UHMW polymers from sources such as W.I. Gore & Associates, Flagstaff, Ariz., or Porex Technologies, Fairburn, Ga., or DeWAL Industries, Saunderstown, R.I. It is appreciated that other hydrophobic materials may be used as well.

Figure 10A:
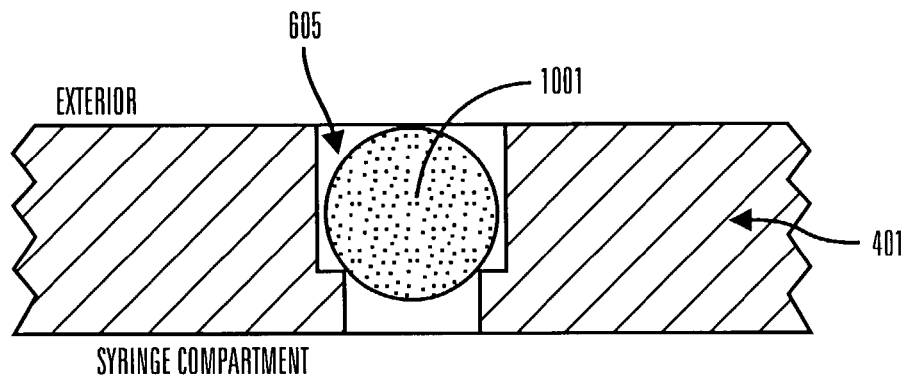
FIGS. 10a, 10b and 10c are cross-sectional views of various embodiments of venting ports for use with the drive mechanism of FIG. 4.
Figure 10B:
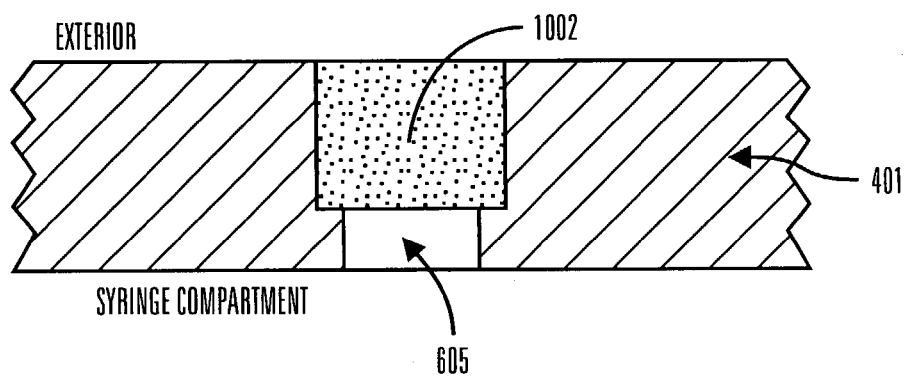
Figure 10C:
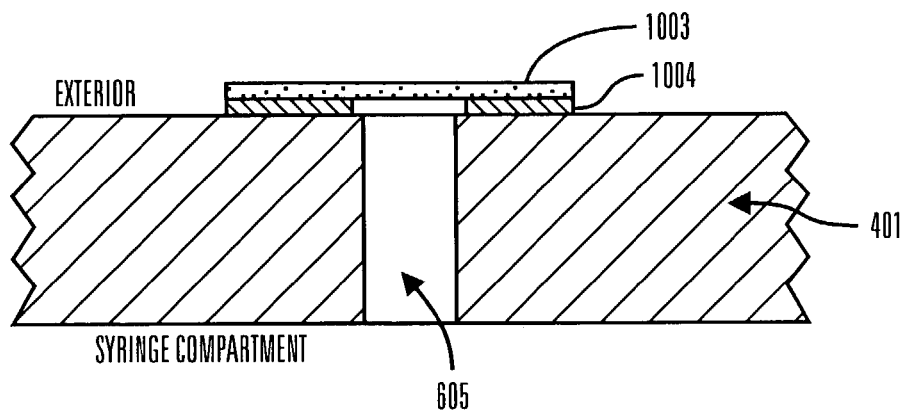

These materials are available in sheet form or molded (press and sintered) in a geometry of choice. Referring to FIGS. 10a–10c, preferred methods to attach this material to the housing 401 include molding the hydrophobic material into a sphere 1001 (FIG. 10a) or a cylinder 1002 (FIG. 10b) and pressing it into a cavity in the pre-molded plastic housing. Alternatively, a label 1003 (FIG. 10c) of this material could be made with either a transfer adhesive or heat bond material 1004 so that the label could be applied over the vent port 605. Alternatively, the label could be sonically welded to the housing. In either method, air will be able to pass freely, but water will not.

In an alternative embodiment (not shown), the vent port could be placed in the connector 431 which secures the reservoir 406 to the housing 401 and which also serves to secure and connect the reservoir 406 to the infusion set tubing (not shown). As described in greater detail in co-pending U.S. patent application Ser. No. 09/428,818 filed on Oct. 28, 1999, which application is incorporated by reference in its entirety, the connector and infusion set refers to the tubing and apparatus which connects the outlet of the reservoir to the user of a medication infusion pump.

An advantage of placing the vent port and hydrophobic material in this location, as opposed to the housing 401, is that the infusion set is disposable and is replaced frequently with each new reservoir or vial of medication. Thus new hydrophobic material is frequently placed into service. This provides enhanced ventilation as compared with the placement of hydrophobic material in the housing 401. Material in this location will not be replaced as often and thus is subject to dirt or oil build up which may retard ventilation. In yet another alternative embodiment however, vent ports with hydrophobic material could be placed in both the pump housing and in the connector portion of the infusion set.

Figure 11:
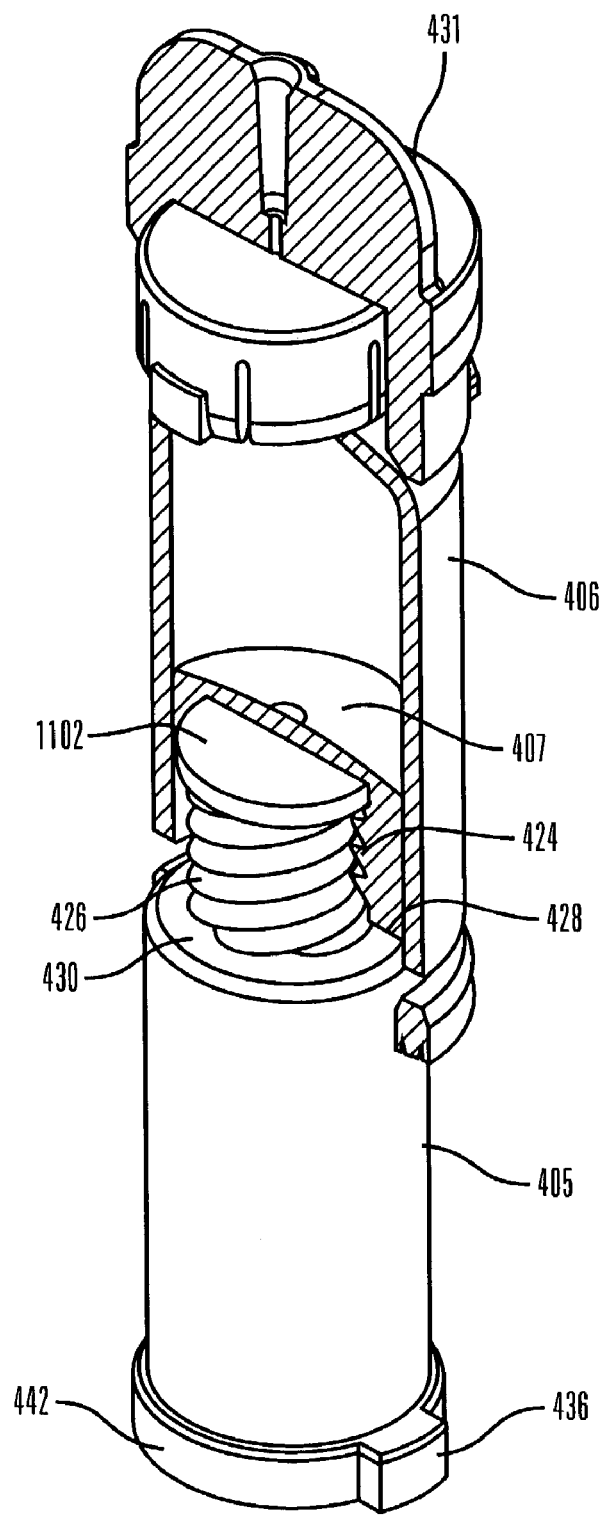
FIG. 11 is a partial, cross-sectional view of a reservoir and plunger slide assembly.

Regardless of the location of the vent port, there remains the possibility that the vent port can become clogged by the accumulation of dirt, oil, etc. over the hydrophobic material. In another feature of certain embodiments of the present invention, the releasable coupler can act to prevent unintentional medication delivery in those instances when the internal pump housing pressure exceeds atmospheric pressure. Referring to FIG. 11, the coupler includes threads formed in a cavity within the external face of the reservoir piston assembly 407. The threaded cavity 424 engages the threads of the male portion 426 which in turn is attached to the end 430 of the plunger slide 405.

This thread engagement reduces or prevents the effect of atmospheric pressure differentials acting on the water resistant, air-tight housing 401 (not shown in FIG. 11) from causing inadvertent fluid delivery. The threads of the male portion 426 act to inhibit or prevent separation of the reservoir piston assembly 407 from the plunger slide 405 which, in turn, is secured to the drive screw 404 (not shown in FIG. 11) by engagement of the external threads of the drive screw 404 with the internal threads of the plunger slide 405. As a result, the coupler resists movement of the reservoir piston assembly 407 caused by atmospheric pressure differentials.

When the reservoir 406 is to be removed, it is twisted off of the coupler male portion 426. The system electronics then preferably cause the drive motor 403 to rapidly rewind so that the plunger slide 405 is driven into a fully retracted position (FIGS. 4 and 6). A new reservoir 406, however, may not be full of fluid. Thus the reservoir piston assembly 407 may not be located in the furthest possible position from the reservoir outlet. Should the reservoir piston assembly 407 be in such an intermediate position, then it may not be possible to engage the threads of the male portion 426 of the coupler (which is in a fully retracted position) with those in the female portion 424 of the coupler in the reservoir piston assembly 407 upon initial placement of the reservoir.

In accordance with another feature of certain embodiments, the illustrated embodiment provides for advancement of the plunger slide 405 upon the insertion of a reservoir into the pump housing. The plunger slide 405 advances until it comes into contact with the reservoir piston assembly 407 and the threads of the coupler male portion 426 of the coupler engage the threads in the female portion 424 in the reservoir piston assembly 407. When the threads engage in this fashion in the illustrated embodiment, they do so not by twisting. Rather, they rachet over one another.

In the preferred embodiment, the threads of the coupler male portion 426 have a 5 start, 40 threads per inch ("TPI") pitch or profile while the threads of the coupler female portion 424 have a 2 start, 40 TPI pitch or profile as illustrated in FIG. 11. Thus these differing thread profiles do not allow for normal tooth-to-tooth thread engagement. Rather, there is a cross threaded engagement.

The purpose of this intentional cross threading is to reduce the force necessary to engage the threads as the plunger slide 405 seats into the reservoir piston assembly 407. In addition, the 2 start, 40 TPI threads of the coupler female portion 424 are preferably made from a rubber material to provide a degree of compliance to the threads. On the other hand, the 5 start, 40 TPI threads of the male coupler portion 426 are preferably made of a relatively hard plastic. Other threading arrangements and profiles could be employed resulting in a similar effect.

Figure 13A:
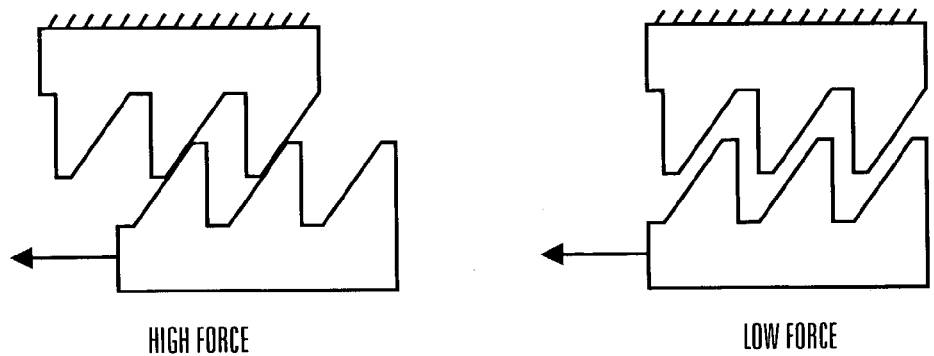
FIGS. 13a and 13b are plunger slide force profile diagrams.
Figure 13A:
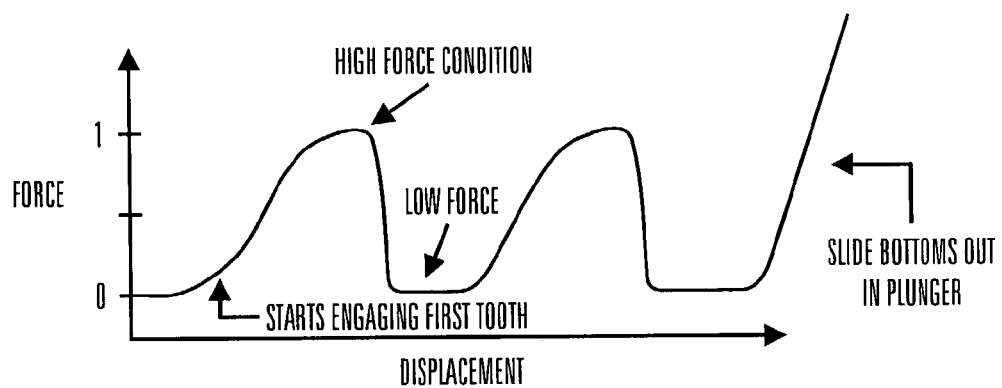

If on the other hand, the threads had a common thread pitch with an equal number of starts given the same degree of thread interference (i.e., the OD of the male feature being larger than the OD of the female feature), then the force needed to insert the male feature would be pulsatile. Referring to FIG. 13a, as each thread tooth engages the next tooth, the insertion force would be high as compared to the point where the thread tooth passes into the valley of the next tooth. But with the cross threaded arrangement of the preferred embodiment, not all of the threads ride over one another at the same time. Rather, they ratchet over one another individually due to the cross-threaded profile. This arrangement results in less force required to engage the threads when the plunger slide moves axially, but still allows the reservoir to easily be removed by a manual twisting action.

While the advantage of utilizing a common thread pitch would be to provide a maximum ability to resist axial separation of the reservoir piston assembly 407 from the plunger slide 405, there are disadvantages. In engaging the threads, the peak force is high and could result in excessive delivery of fluids as the plunger slide 405 moves forward to seat in the cavity of the reservoir piston assembly 407. As described in greater detail in co-pending U.S. patent application Ser. No. 09/428,411 filed on Oct. 28, 1999, which application is incorporated by reference in its entirety, the pump may have an occlusion detection system which uses axial force as an indicator of pressure within the reservoir. If so, then a false alarm may be generated during these high force conditions.

It is desirable therefore to have an insertion force profile which is preferably more flat than that shown in FIG. 13a. To accomplish this, the cross threading design of the preferred embodiment causes the relatively soft rubber teeth of the female portion 424 at the end of the reservoir piston assembly 407 to rachet or swipe around the relatively hard plastic teeth of the coupler resulting in a significantly lower insertion force for the same degree of thread interference (See FIG. 13b). This is due to the fact that not all of the thread teeth ride over one another simultaneously. Moreover, the cross-sectional shape of the threads are ramped. This makes it easier for the threads to ride over one another as the plunger slide is being inserted into the reservoir piston. However, the flat opposite edge of the thread profile makes it much more difficult for the plunger slide to be separated from the reservoir piston.

Figure 13B:
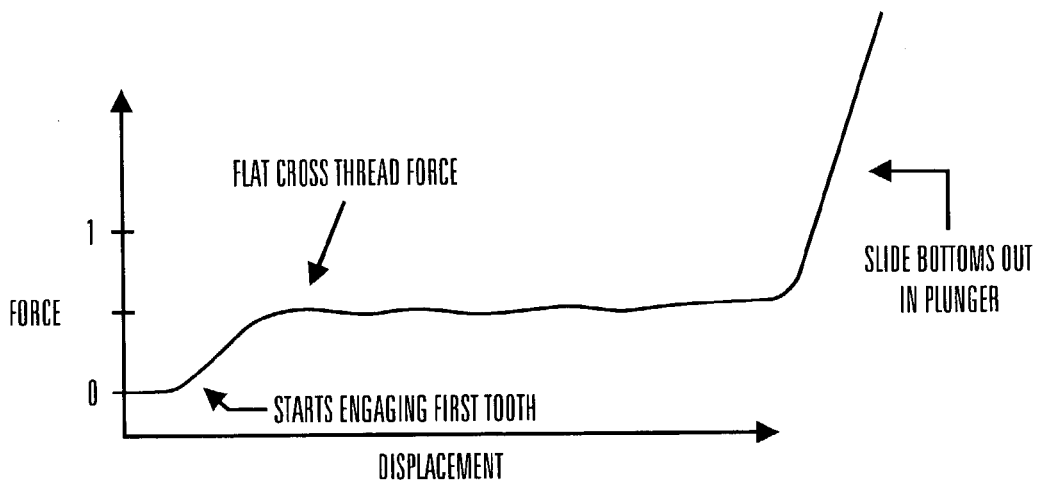

When the plunger slide is fully inserted into the reservoir piston, the slide bottoms out in the cavity of the piston. At this point the presence of the hydraulic load of the fluid in the reservoir as well as the static and kinetic friction of the piston will act on the plunger slide. FIG. 13b shows the bottoming out of the plunger slide against a piston in a reservoir having fluid and the resulting increase in the axial force acting on the piston and the plunger slide. This hydraulic load in combination with the static and kinetic friction is so much higher than the force required to engage the piston threads that such a disparity can be used to advantage.

Figure 2:
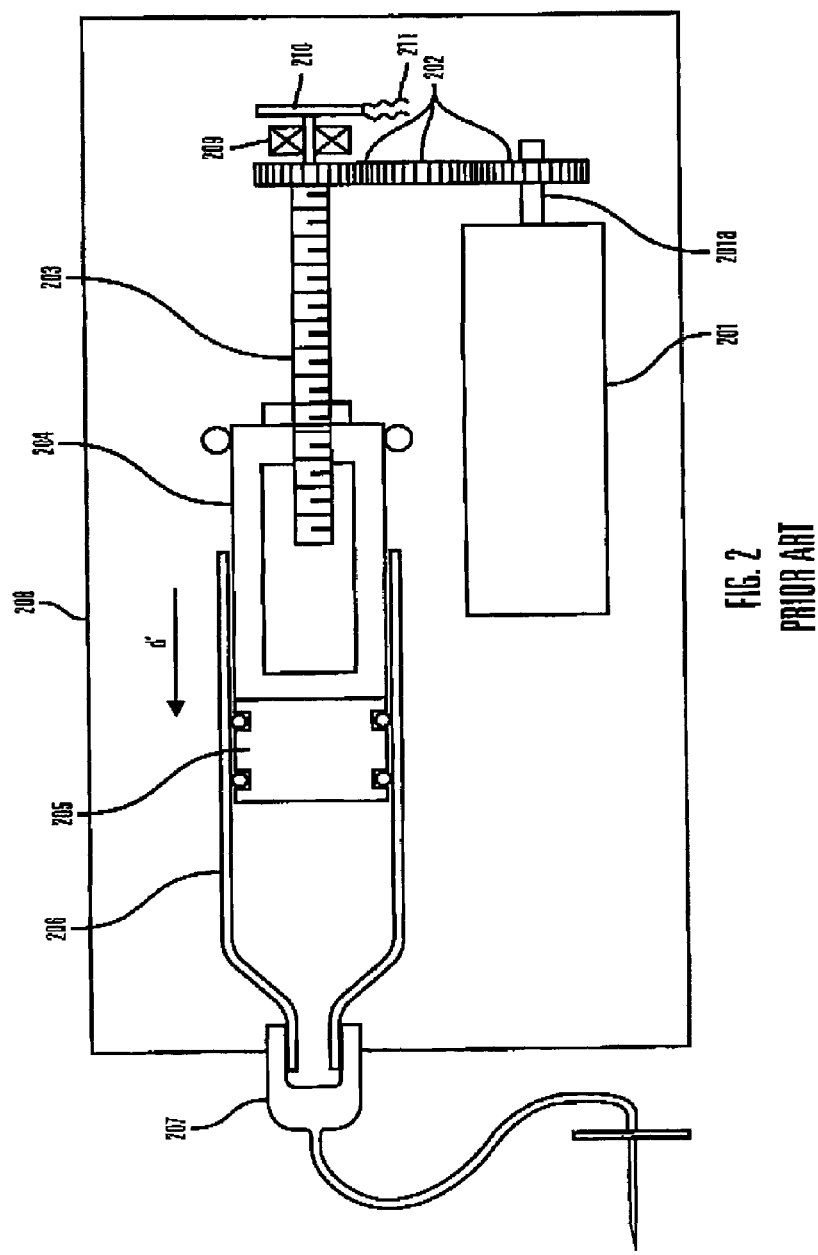
FIG. 2 is a side plan view of a another conventional lead-screw drive mechanism.
Figure 3A:
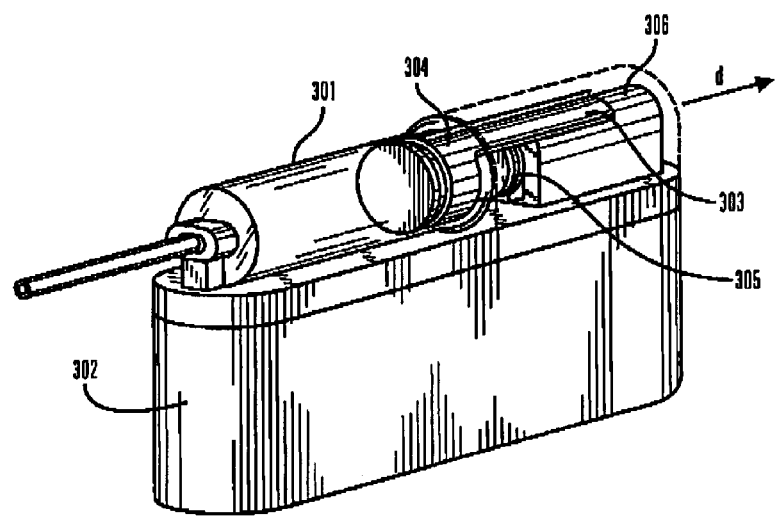
FIG. 3a is a perspective view of another conventional lead-screw drive mechanism.
Figure 3B:
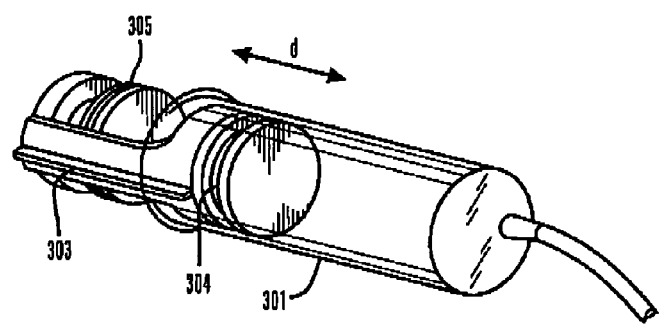

The fluid pressure and occlusion detection systems described in U.S. Provisional Patent Application Serial No. 60/243,392 filed Oct. 26, 2000, or in co-pending U.S. patent application Ser. No. 09/428,411 filed Oct. 28, 1999, both of which are incorporated herein by reference in their entireties, or known pressure switch detectors, such as those shown and described with reference to FIGS. 1 and 2, can be used to detect the fluid back pressure associated with the bottoming out of the plunger slide against the piston. A high pressure trigger point of such a pressure switch or occlusion detection system can be set at a point above the relatively flat cross thread force as shown in FIG. 13b. Alternatively, the ramping or the profiles of such back pressure forces can be monitored. When an appropriate limit is reached, the pump system electronics can send a signal to stop the pump motor. Thus the pump drive system is able to automatically detect when the plunger slide has bottomed out and stop the pump motor from advancing the plunger slide.

Figure 12:
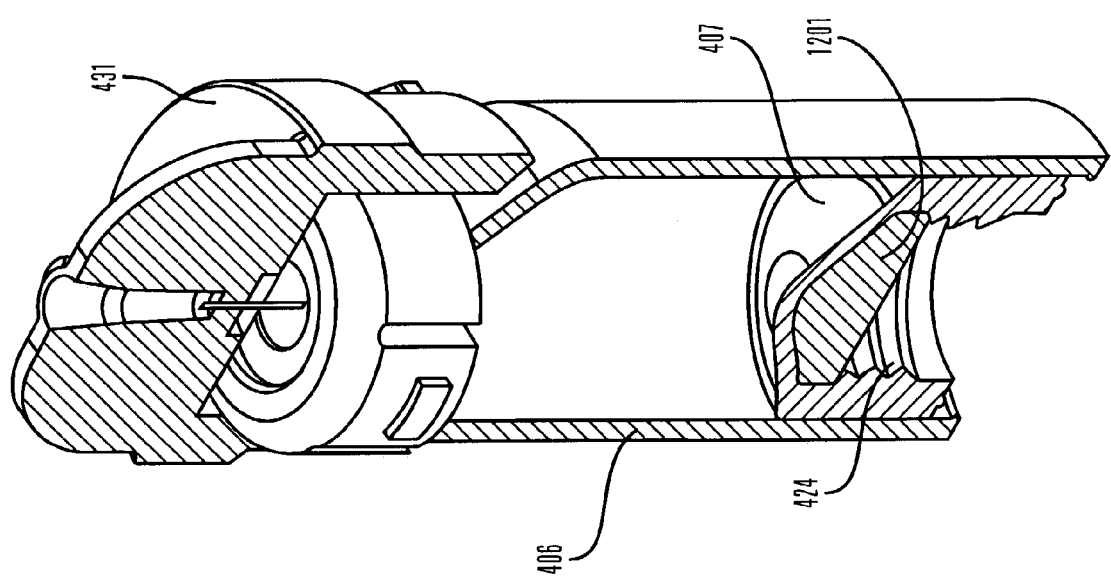
FIG. 12 is a partial, cross sectional view of a reservoir and a reservoir connector.

Referring to FIGS. 11 and 12, the 5 start, 40 TPI (0.125" lead) thread profile of the coupler male portion 426 was chosen in consideration of the thread lead on the preferred embodiment of the connector 431. The connector 431 is secured into the pump housing with threads 433 (FIG. 7b) having a 2 start, 8 TPI (0.250" lead) profile. Therefore the 0.250" lead on the connector is twice that of the reservoir piston assembly 407 which is 0.125". This was chosen to prevent inadvertent fluid delivery during removal of the reservoir from the pump housing, or alternatively, to prevent separation of the reservoir piston assembly 407 from the reservoir 406 during removal from the pump housing. When the connector 431 is disengaged from the pump, the connector 431 as well as the reservoir 406 will both travel with the 0.250" lead. Since the threaded coupler lead is 0.125", the plunger slide 405 will disengage somewhere between the 0.125" lead of the threaded coupler and the 0.250" lead of the infusion set 1103. Therefore, the rate that the reservoir piston assembly 407 is removed from the pump is the same down to half that of the reservoir 406/connector 431. Thus any medication which may be present in the reservoir 406 will not be delivered to the user. Additionally, the length of the reservoir piston assembly 407 is sufficient such that it will always remain attached to the reservoir 406 during removal from the pump. Although the preferred embodiment describes the plunger slide 405 having a coupler male portion 426 with an external thread lead that is different from the connector 431, this is not necessary. The thread leads could be the same or of an increment other than what has been described.

The 2 start thread profile of the coupler female portion 424 on the reservoir piston assembly 407 of the preferred embodiment provides another advantage. Some versions of these reservoirs may be designed to be filled by the user. In such an instance, a linear actuation member comprising a handle (not shown) will need to be screwed into the threaded portion of the reservoir piston assembly 407 in order for the user to retract the reservoir piston assembly 407 and fill the reservoir. The number of rotations necessary to fully insert the handle depends upon the distance the handle thread profile travels to fully engage the reservoir piston assembly 407 as well as the thread lead.

For example, a single start, 40 TPI (0.025" lead) thread requires 4 complete rotations to travel a 0.10" thread engagement. However, a 2 start, 40 TPI (0.050" lead) thread only requires 2 complete rotations to travel the 0.10" thread engagement. Therefore, an additional advantage of a 2 start thread as compared to a single start thread (given the same pitch) is that half as many rotations are needed in order to fully seat the handle.

In alternative embodiments which are not shown, the end of the plunger slide 405 may include a détente or ridge to engage with a corresponding formation in the reservoir piston assembly 407 to resist unintended separation of the plunger slide 405 from the reservoir piston assembly 407. In other embodiments, the plunger slide 405 is inserted and removed by overcoming a friction fit. Preferably, the friction fit is secure enough to resist movement of the reservoir piston assembly 407 relative to the plunger slide 405 due to changes in air pressure, but low enough to permit easy removal of the reservoir 406 and its reservoir piston assembly 407 from the plunger slide 405 once the fluid has been expended. In other embodiments, the détente or ridge may be spring loaded or activated to grasp the reservoir piston assembly 407 once the drive mechanism has been moved forward (or extended), but is retracted by a switch or cam when the drive mechanism is in the rearmost (or retracted) position. The spring action could be similar to those used on collets. In other embodiments of the inventions, the threaded coupler may be engaged with the threaded cavity of the reservoir piston by twisting or rotating the reservoir as it is being manually placed into the housing.

As previously mentioned, some pump systems may have an occlusion detection system which uses the axial force on the drive train as an indicator of pressure within a reservoir. One problem faced by such occlusion detection systems, however, is the system compliance associated with reservoir fluid back pressures. As previously mentioned, the force on a piston assembly resulting from increased back pressures can deform a piston which is constructed of relatively flexible material such as rubber. Should an occlusion arise in the fluid system, this deformation can reduce the rate at which fluid back pressures increase. This in turn can increase the amount of time required for the system to detect an occlusion—a situation which may be undesirable.

To address this problem, an insert 1201 which is made of hard plastic, stainless steel or other preferably relatively stiff material is disposed in the upper portion of the reservoir piston assembly 407. (FIG. 12) The insert 1201 of the illustrated embodiment provides stiffness to the rubber reservoir piston assembly 407. This can reduce undesirable compliance which is associated with the reservoir.

Figure 14:
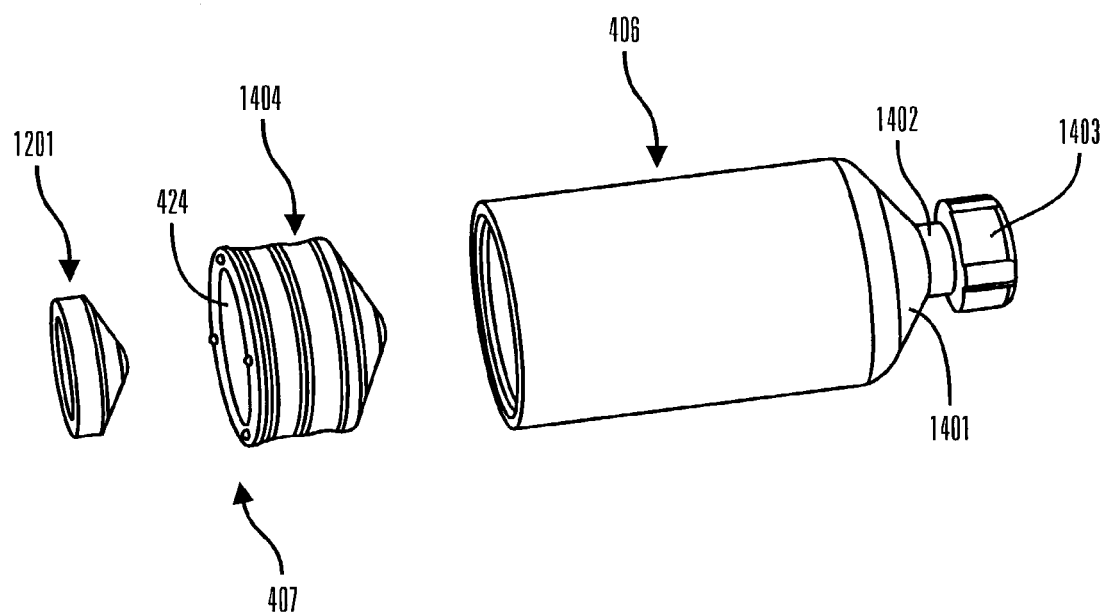
FIG. 14 is an exploded view of a reservoir, a piston, and an insert.

FIG. 14 shows an industry standard reservoir 406 and the piston assembly 407 comprising a piston member 1404 and an insert 1201. One end of the reservoir 406 has a generally conical-shaped end portion 1401 which tapers to a neck 1402. A swage 1403 is secured to the neck thereby forming a fluid-tight seal. The insert 1201 is placed in the cavity 424 of the piston member 1404 which in turn is placed in the opposite end of the reservoir 406.

Figure 15A:
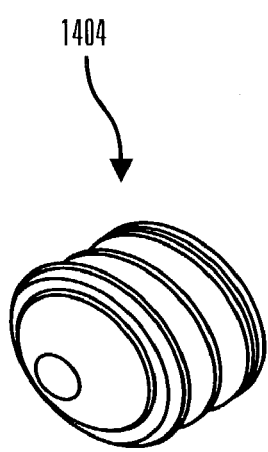
FIG. 15a is a perspective view of a reservoir piston.
Figure 15B:
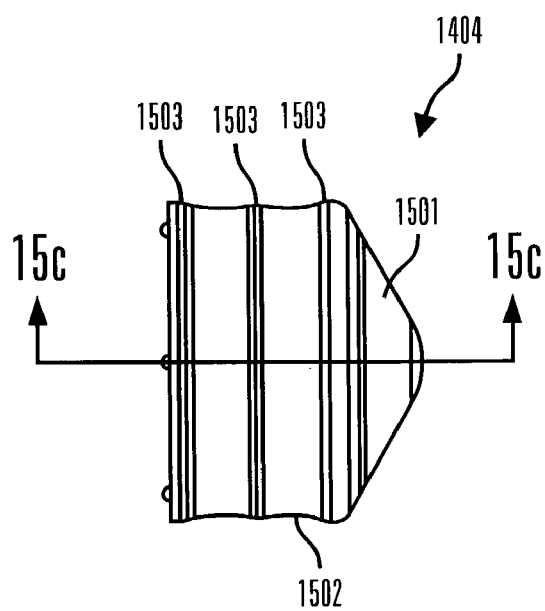

FIGS. 15a and 15b show the piston member 1404 which is adapted to receive the insert 1201 (FIG. 14). The piston member 1404 is further adapted to be slidably mounted within the reservoir 1401 and to form a fluid-tight barrier therein. The exterior of the piston member 1404 includes a generally cylindrical side wall 1502 and an external proximate side 1501 having a generally conical convex shape which is adapted to conform to the conical-shaped end portion 1401 of the reservoir 406 (FIG. 14). This geometry reduces the residual volume of fluid remaining in the reservoir 406 after the piston assembly 407 is fully advanced. The piston member's side wall 1502 has a plurality of ridges 1503 which form a friction fit with the interior of the reservoir side wall thereby forming a fluid-resistant seal.

Figure 15C:
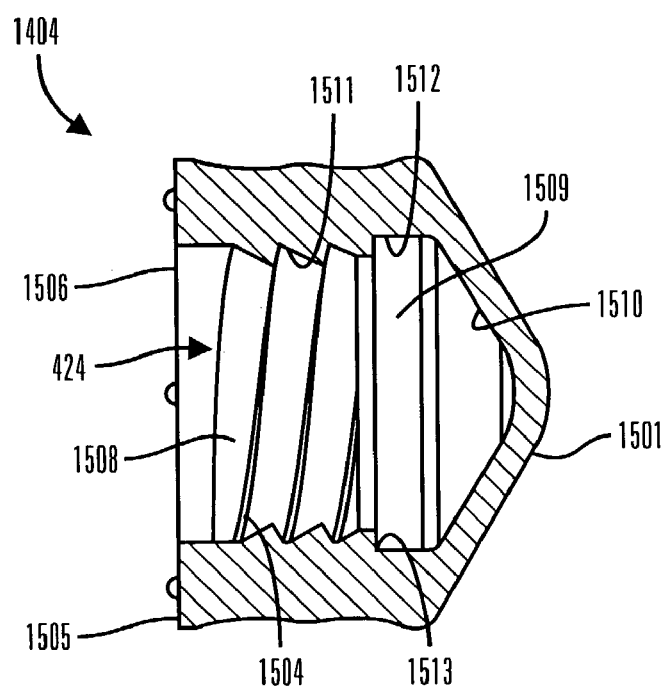
FIG. 15c is a cross-sectional view of the piston along lines 15c—15c of FIG. 15b.

Referring to FIG. 15c, the piston member 1404 has an external distal side 1505 which is opposite to the external proximate side 1501 which in turn is adapted to contact any fluid which might be present in the reservoir. The external distal side 1505 has an opening 1506 leading into the threaded cavity 424. The cavity 424 comprises a first chamber 1508 extending from the external distal side 1505 into the cavity 424 and a second chamber 1509 extending from the first chamber 1508 to an internal proximate wall 1510 which is disposed adjacent to the external proximate side 1501 of the piston member 1404.

The first chamber 1508 is defined by a generally cylindrically-shaped first wall 1511 extending axially from the external distal side 1505 into the cavity 424. The first wall 1511 includes threads 1504 formed on the wall which are adapted to couple with any linear actuator member, such as for example, the threads of the male portion 426 of the plunger slide 405 as previously described (FIG. 11). The second chamber 1509 is defined by a generally cylindrically-shaped second wall 1512 extending axially from the generally cylindrically-shaped first wall 1511 into the cavity 424 and by the internal proximate wall 1510. The generally cylindrically-shaped second wall 1512 has a radius which is greater than that of the generally cylindrically-shaped first wall 1511. A ledge 1513 extends from the generally cylindrically-shaped first wall 1511 to the generally cylindrically-shaped second wall 1512. The internal proximate wall 1510 forms the end of the second chamber 1509 and is generally concave conical in shape. Thus the thickness of that portion of the first member which is between the internal proximate wall 1510 and the external proximate side 1501 is generally uniform.

Figure 16A:
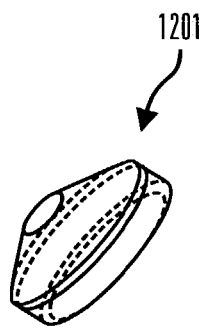
FIG. 16a is a perspective view of a piston insert.
Figure 16B:
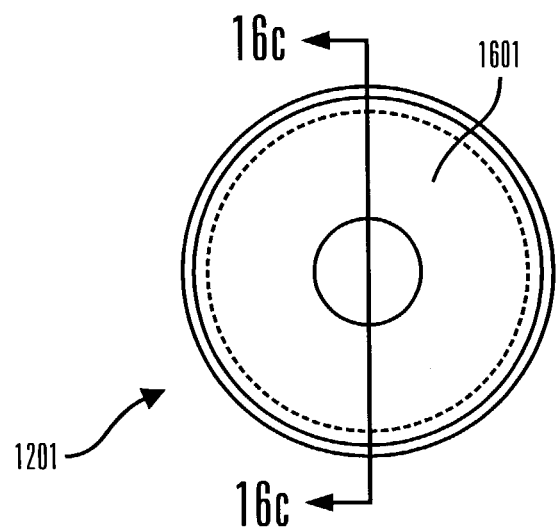
Figure 16C:
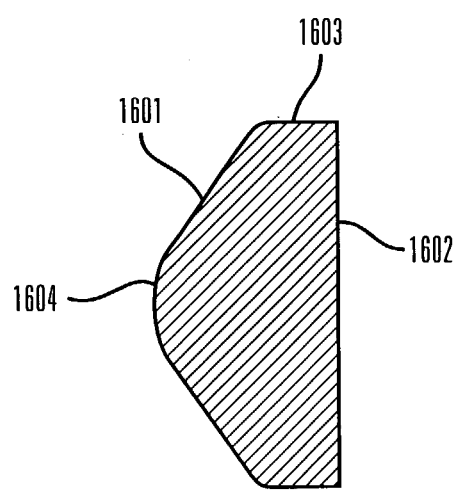
FIG. 16c is a cross-sectional view of the insert along lines 16c—16c of FIG. 16b.

Referring to FIGS. 16a–16c, the insert 1201 is a solid member which has a planar back wall 1602, a generally cylindrical side wall 1603, and a conical face portion 1601 which terminates in a spherically-shaped end portion 1604. In one embodiment, the planar back wall 1602 is 0.33 inches in diameter, the cylindrical side wall 1603 is approximately 0.054 inches in length, the conical face portion 1601 is approximately 0.128 inches in length, and the spherically-shaped end portion 1604 has a radius of curvature of approximately 0.095 inches.

The face portion 1601 and the end portion 1604 are adapted to mate with the internal proximate wall 1510 and the back wall 1602 is adapted to seat against the ledge 1513 of the piston member 1404 (FIG. 15c). When inserted, the insert face portion 1601 and the external proximate side 1501 are in a generally parallel spaced-apart relationship. The insert 1201 is a relatively incompressible member which can be made of stainless steel or relatively stiff plastic or any other material which preferably has stiffness properties which are greater than that of the external proximate side 1501 of the piston member 1404. If a hard plastic material is selected, however, it preferably should be a grade of plastic which can withstand the high temperatures associated with an autoclave.

Figure 17:
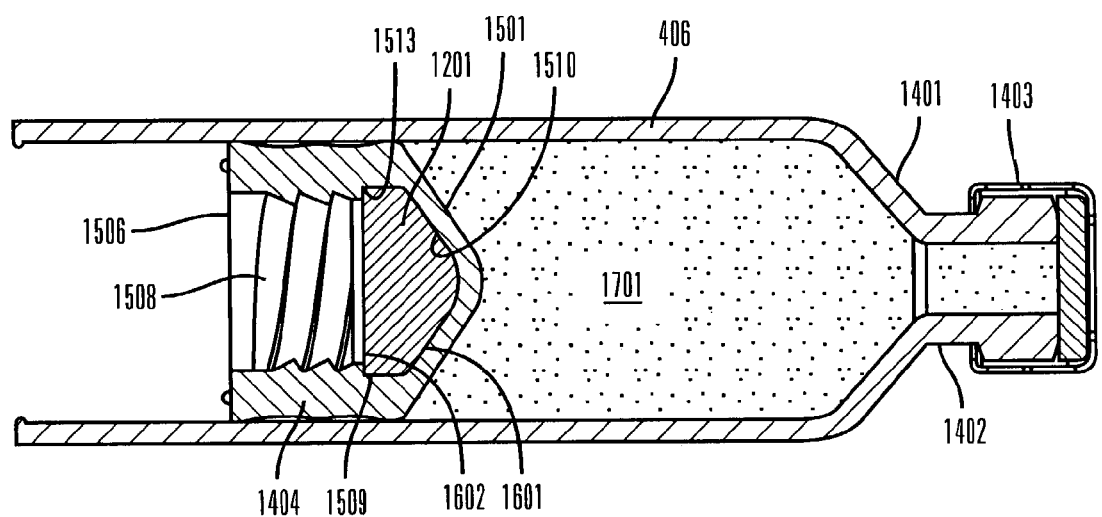
FIG. 17 is a cross-sectional view of a reservoir, reservoir piston, and insert.

FIG. 17 shows the reservoir 406 with the piston member 1404 and the insert 1201 as assembled. As previously mentioned, the ledge 1513 supports the planar back 1602 of the insert 1201 and secures it into place. Because the piston member 1404 is constructed of rubber or other relatively flexible material, it can deflect sufficiently during assembly to permit the insert 1201 to be inserted in the opening 1506 and through the first chamber 1508 and then positioned in the second chamber 1509. The conical face portion 1601 of the insert 1201 mates with the internal proximate wall 1510 of the piston member 1404 thus permitting a reduced thickness of rubber which is in direct contact with fluid 1701. This reduced thickness of rubber or other flexible material minimizes the compliance which might otherwise be caused by the back pressure of the fluid 1701 acting on the external proximate side 1501 of the piston member 1404.

It should be appreciated that although the insert member 1201 depicted in FIGS. 14–17 is removable from the piston member 1404, alternative embodiments of the present invention include a piston assembly in which there are no openings or open cavities and in which an insert member is encased in such a manner so as to be not removable.

Figure 18:
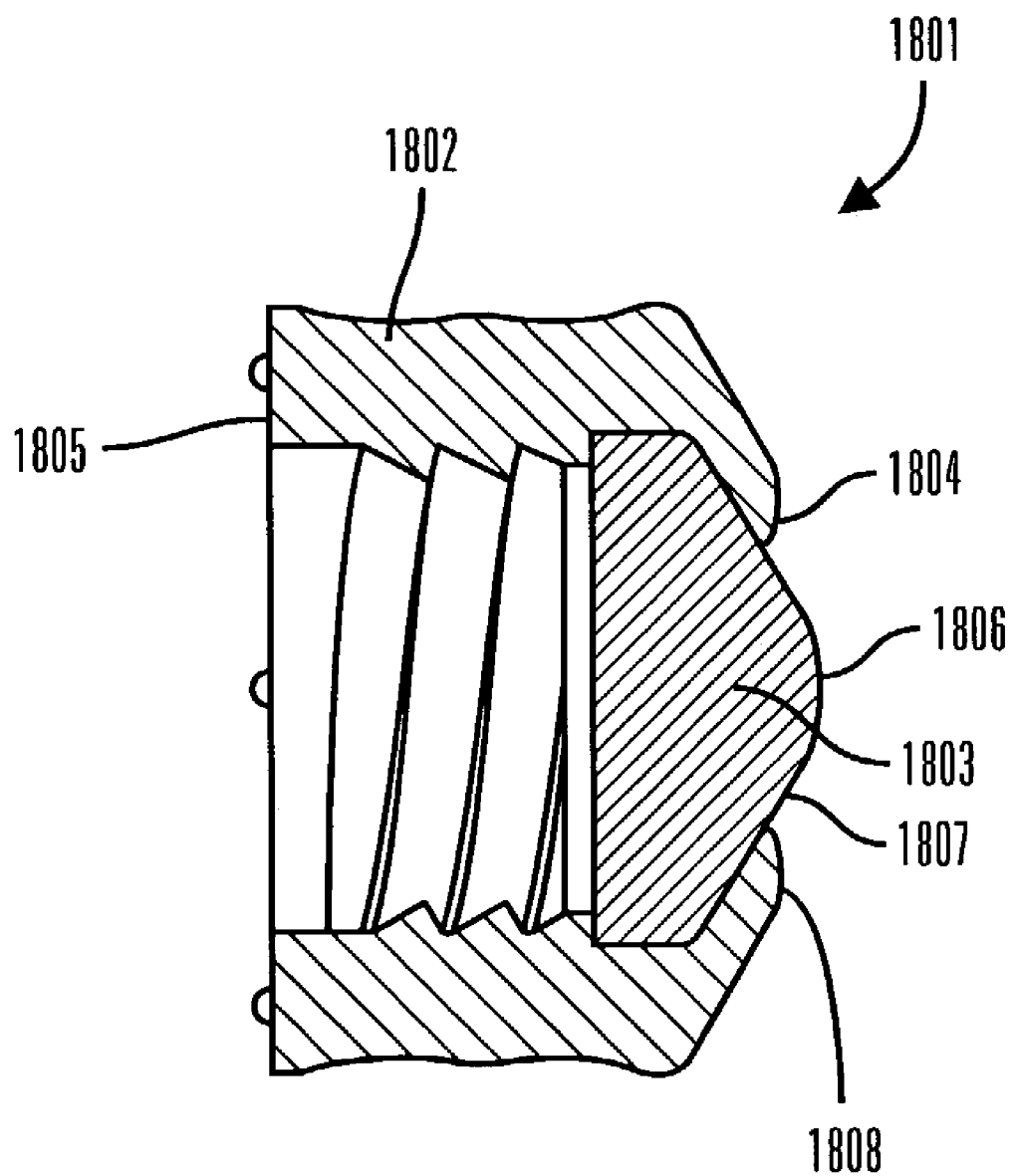
FIG. 18 is a cross-sectional view of a piston and piston insert according to an alternative embodiment of the present invention.

The insert member of the above-described embodiments is not adapted to contact the fluid in a reservoir. However, FIG. 18 shows yet another alternative embodiment where a portion of an insert member is adapted to contact reservoir fluid. A piston assembly 1801 comprises a piston member 1802 and an insert 1803. The piston member 1802 is adapted to be slidably mounted within a reservoir (not shown in FIG. 18) and is further adapted to form part of a fluid-tight barrier within the reservoir. The piston member 1802 has an external proximate side 1804 and an external distal side 1805. The external proximate side 1804 is adapted to contact the reservoir fluid and is made of an elastomeric material, such as rubber.

The insert 1803 is substantially contained within the piston member 1802 and has a face 1806 which is made of a material, such as stainless steel or hard plastic, having a stiffness which is greater than that of the piston member 1802. The insert face 1806 has an exposed portion 1807 and an enclosed portion 1808. The exposed portion 1807 is adapted to contact the fluid within the reservoir whereas the enclosed portion 1808 is enclosed or covered by the external proximate side 1804 of the piston member 1802. Therefore, the insert 1803 extends past the external proximate side of the piston member 1802 and is adapted for contact with the fluid to complete the fluid-tight barrier within the reservoir. Thus the arrangement of the insert 1803 in this fashion provides the necessary stiffness to the piston assembly 1801 to reduce system compliance.

It should be appreciated that while the piston members and inserts described above include conical geometries, other geometries can be used. For example in an alternative embodiment shown in FIG. 11, an insert 1102 has a disc shape with relatively flat faces. This also can provide the necessary stiffness to the piston assembly 407 to reduce system compliance.

In yet further embodiments (not shown), an insert member is an integral part of a male portion of a plunger slide assembly which is adapted to fit within a piston assembly cavity. The male portion of the slide assembly (i.e., the insert member) is further adapted to abut an internal proximate wall within the cavity thus providing increased stiffness to that portion of the piston assembly which is in contact with reservoir fluid.

It can be appreciated that the design of FIGS. 4–18 results in an arrangement where the plunger slide 405 is reliably but releasably coupled to the drive screw 404. When it is time to replace the reservoir 406, it can be detached from the male end of the coupler without affecting the plunger/drive screw engagement. Moreover in one embodiment, the plunger slide 405 is shaped as a hollow cylinder with internal threads. Thus it completely encircles and engages drive screw 404. When the plunger slide 405 is in a relatively retracted position, it encloses any gears which couple the motor 403 with the drive screw 404 thus achieving an extremely compact design. A vent port covered with-hydrophobic material as well as a threaded coupler provide redundant means for permitting exposure of the pump to changing atmospheric pressures without the unintended delivery of medication. A reservoir piston assembly 407 includes an insert member 1201 which increases the stiffness of the piston assembly 407 thus reducing fluid system compliance.

While the description above refers to particular embodiments of the present inventions, it will be understood that many modifications may be made without departing from the spirit thereof. The accompanying claims are intended to cover such modifications as would fall within the true scope and spirit of the present inventions. The presently disclosed embodiments are therefore to be considered in all respects as illustrative and not restrictive, the scope of the inventions being indicated by the appended claims rather than the foregoing description, and all changes which come within the meaning and range of equivalency of the claims are therefore intended to be embraced therein.

What is claimed is:

1. An apparatus for dispensing a medication fluid from a reservoir adapted to contain the fluid, the apparatus comprising:
    a reservoir cavity adapted to receive the reservoir;
    a drive system;
    at least one plunger slider having one end coupled to the drive system and the other end releasably coupled to the reservoir, wherein the at least one plunger slider is adapted to translate from a retracted position to an extended position to dispense the fluid from the reservoir in response to actuation by the drive system;
    a sealing ring mounted around the at least one plunger slider; and
    a spring disposed within the sealing ring, wherein the sealing ring with the spring disposed therein is adapted to allow the at least one plunger slider to translate from the retracted position to the extended position and to prevent entry of fluid from the reservoir cavity into the drive system.

2. The apparatus of claim 1, wherein the sealing ring is formed from Teflon.

3. The apparatus of claim 1, wherein the sealing ring is formed from plastic.

4. The apparatus of claim 1, wherein the spring is a leaf spring.

5. The apparatus of claim 1, wherein the spring is a canted coil spring.

6. The apparatus of claim 1, wherein the sealing ring has a proximate side and a distal side, the proximate side being adjacent to the reservoir cavity, and the distal side defining an opening leading into a cavity, wherein the spring is inserted into the cavity in the sealing ring.

7. The apparatus of claim 1, wherein the sealing ring has a proximate side and a distal side, the proximate side being adjacent to the reservoir cavity and defining an opening leading into a cavity, wherein the spring is inserted into the cavity in the sealing ring.

8. The apparatus of claim 1, wherein the spring is enclosed within the sealing ring.

9. The apparatus of claim 1, wherein the drive system comprises:
    a drive motor; and
    a drive gear positioned to be rotatably actuated by the drive motor, said drive gear having external threads;
    wherein the at least one plunger slider has internal threads positioned to be engaged by the external threads of the drive gear and is adapted to be linearly actuated by rotation of the external threads of the drive gear.

10. The apparatus of claim 1, wherein the drive system comprises:
    a drive motor having a rotating drive shaft; and
    a gearbox coupled to the drive shaft of the drive motor; and
    wherein the at least one plunger slider is coupled to the gearbox and adapted to translate from the refracted position to the extended position in response to rotation of the drive shaft of the drive motor.

11. The apparatus of claim 10, wherein the at least one plunger slider substantially radially surrounds at least a portion of a length of the gearbox when the at least one plunger slider is in the refracted position.

12. An apparatus for dispensing a medication fluid from a reservoir adapted to contain the fluid, the apparatus comprising:
    a reservoir cavity adapted to receive the reservoir;
    a drive motor;
    a drive gear coupled to the drive motor and adapted to be rotatably actuated by the drive motor;
    at least one plunger slider having one end coupled to the drive gear and the other end releasably coupled to the reservoir, wherein the at least one plunger slider is adapted to be linearly actuated from a retracted position to an extended position to dispense the fluid from the reservoir in response to rotation by the drive gear;
    a sealing ring mounted around the at least one plunger slider; and
    a spring disposed within the sealing ring, wherein the sealing ring with the spring disposed therein is adapted to allow the at least one plunger slider to translate from the refracted position to the extended position and to prevent entry of fluid from the reservoir cavity into the drive system.

13. The apparatus of claim 12, wherein the sealing ring is formed from Teflon.

14. The apparatus of claim 12, wherein the sealing ring is formed from plastic.

15. The apparatus of claim 12, wherein the spring is a leaf spring.

16. The apparatus of claim 12, wherein the spring is a canted coil spring.

17. The apparatus of claim 12, wherein the sealing ring has a proximate side and a distal side, the proximate side being adjacent to the reservoir cavity, and the distal side defining an opening leading into a cavity, wherein the spring is inserted into the cavity in the sealing ring.

18. The apparatus of claim 12, wherein the sealing ring has a proximate side and a distal side, the proximate side being adjacent to the reservoir cavity and defining an opening leading into a cavity, wherein the spring is inserted into the cavity in the sealing ring.

19. The apparatus of claim 12, wherein the spring is enclosed within the sealing ring.

20. The apparatus of claim 12, wherein the drive gear has external threads, and wherein the at least one plunger slider has internal threads positioned to be engaged by the external threads of the drive gear and is adapted to be linearly actuated by rotation of the external threads of the drive gear.

* * * * *